United States Patent
Woolfson et al.

(10) Patent No.: US 10,342,657 B2
(45) Date of Patent: Jul. 9, 2019

(54) FIXATION BAND FOR AFFIXING A PROSTHETIC HEART VALVE TO TISSUE

(71) Applicant: Medtronic, Inc., Minneapolis, MN (US)

(72) Inventors: Steven B. Woolfson, Boston, MA (US); Richard B. Streeter, Winchester, MA (US); Daniel C. Taylor, Brighton, MA (US); John R. Liddicoat, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 72 days.

(21) Appl. No.: 15/367,897

(22) Filed: Dec. 2, 2016

(65) Prior Publication Data

US 2017/0079778 A1    Mar. 23, 2017

Related U.S. Application Data

(60) Continuation of application No. 12/587,041, filed on Oct. 1, 2009, now Pat. No. 9,539,088, which is a
(Continued)

(51) Int. Cl.
*A61F 2/24*       (2006.01)
*A61F 2/848*      (2013.01)

(52) U.S. Cl.
CPC .............. *A61F 2/2409* (2013.01); *A61F 2/24* (2013.01); *A61F 2/2412* (2013.01);
(Continued)

(58) Field of Classification Search
CPC ............ A61F 2/07–2424; A61F 2/2475; A61F 2220/0008–0016; A61F 2/848–2002/8486; A61F 2250/0069
See application file for complete search history.

(56) References Cited

U.S. PATENT DOCUMENTS 3,143,742 A    8/1964 Cromie
3,334,629 A    8/1967 Cohn
(Continued)

FOREIGN PATENT DOCUMENTS

CN    2007-100074433    8/2007
DE        3640745        6/1987
(Continued)

OTHER PUBLICATIONS

"Flange", Collins English Dictionary, pp. 1-6, date accessed Mar. 19, 2018, https://www.collinsdictionary.com/dictionary/english/flange.*
(Continued)

*Primary Examiner* — Yashita Sharma
*Assistant Examiner* — Rebecca S Preston

(57) ABSTRACT

A prosthetic heart comprising a tube having proximal and distal ends, and a central lumen, a tubular frame having proximal and distal ends, and a central lumen, the tubular frame, comprising a plurality of radially-extending members, being disposed on an outside wall of the tube, the distal end of the tube being everted around the distal end of the tubular frame and extending proximally along the tubular frame and over the radially-extending members, and a valve member attached to the tube.

16 Claims, 34 Drawing Sheets

Related U.S. Application Data division of application No. 11/479,357, filed on Jun. 29, 2006, now Pat. No. 7,611,535, which is a division of application No. 10/414,766, filed on Apr. 16, 2003, now Pat. No. 7,097,659, which is a continuation-in-part of application No. 09/949,061, filed on Sep. 7, 2001, now Pat. No. 6,846,325.

(60) Provisional application No. 60/373,059, filed on Apr. 16, 2002.

(52) U.S. Cl.
CPC ............ *A61F 2/2427* (2013.01); *A61F 2/848* (2013.01); *A61F 2/2403* (2013.01); *A61F 2210/0014* (2013.01); *A61F 2220/0016* (2013.01); *A61F 2220/0025* (2013.01); *A61F 2220/0075* (2013.01); *A61F 2230/0013* (2013.01); *A61F 2250/0039* (2013.01); *A61F 2250/0069* (2013.01)

(56) References Cited

U.S. PATENT DOCUMENTS

| | | |
|---|---|---|
| 3,409,013 A | 11/1968 | Berry |
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,163,955 A * | 11/1992 | Love ................. A61F 2/2412 623/2.15 |
| 5,167,628 A | 12/1992 | Boyles |
| 5,217,483 A | 7/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |

(56) References Cited

U.S. PATENT DOCUMENTS

| | | |
|---|---|---|
| 5,860,996 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,104 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,334,873 B1 * | 1/2002 | Lane .............. A61F 2/2409 623/2.14 |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,485,496 B1 | 11/2002 | Suyker et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton et al. |
| 6,769,434 B2 | 8/2004 | Liddicoat et al. |
| 6,776,785 B1 * | 8/2004 | Yencho .............. A61B 17/0644 606/153 |
| 6,786,925 B1 | 9/2004 | Schoon |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |

(56) References Cited

U.S. PATENT DOCUMENTS

| | | |
|---|---|---|
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,682,390 B2 | 3/2010 | Seguin |
| 7,780,726 B2 | 8/2010 | Seguin |
| 7,806,919 B2 | 10/2010 | Bloom et al. |
| 2001/0002445 A1 | 3/2001 | Vesely |
| 2001/0001314 A1 | 5/2001 | Davison et al. |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Bonhoeffer et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149477 A1* | 8/2003 | Gabbay ............... A61F 2/2418 623/2.14 |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Sequin et al. |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Lobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |

(56) References Cited

U.S. PATENT DOCUMENTS

| | | |
|---|---|---|
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0112422 A1 | 5/2007 | Dehdashtian |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Lobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |

(56) References Cited

U.S. PATENT DOCUMENTS

| | | |
|---|---|---|
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0164006 A1 | 6/2009 | Seguin et al. |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 10 074 | 10/2001 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| FR | 1504329 | 12/1967 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/44313 | 8/2000 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 04/019825 | 3/2004 |
| WO | 04/089250 | 10/2004 |
| WO | 05/004753 | 1/2005 |
| WO | 05/046528 | 5/2005 |
| WO | 06/026371 | 3/2006 |
| WO | 08/047354 | 4/2008 |
| WO | 08/138584 | 11/2008 |
| WO | 08/150529 | 12/2008 |
| WO | 09/002548 | 12/2008 |
| WO | 09/029199 | 3/2009 |
| WO | 09/042196 | 4/2009 |
| WO | 09/045338 | 4/2009 |
| WO | 09/061389 | 5/2009 |
| WO | 09/091509 | 7/2009 |
| WO | 09/111241 | 9/2009 |

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. Volume II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

(56) References Cited

OTHER PUBLICATIONS

Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for off-pump mitral valve replacement," European Journal of Cardio Thoracic Surgery, 28:194-198, 2005.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Pavcnik et al., "Aortic and venous valve for percutaneous insertion," Min. Invas. Ther. & Allied Techol. 2000, vol. 9, pp. 287-292.

* cited by examiner

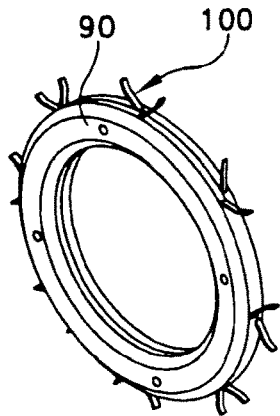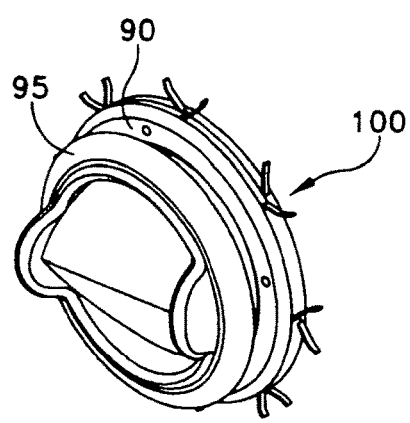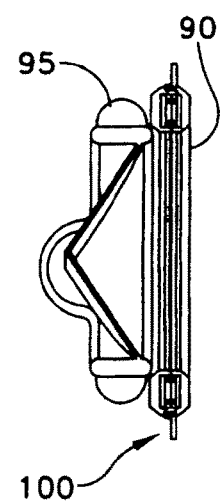
FIG. 9A  FIG. 9B  FIG. 9C
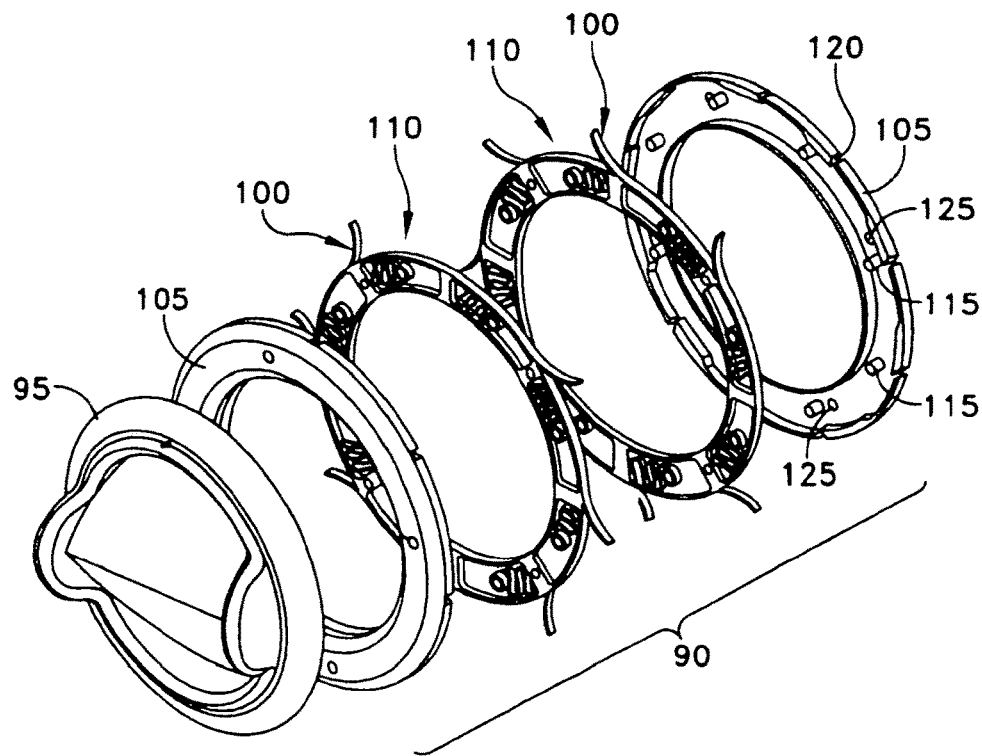
FIG. 9D

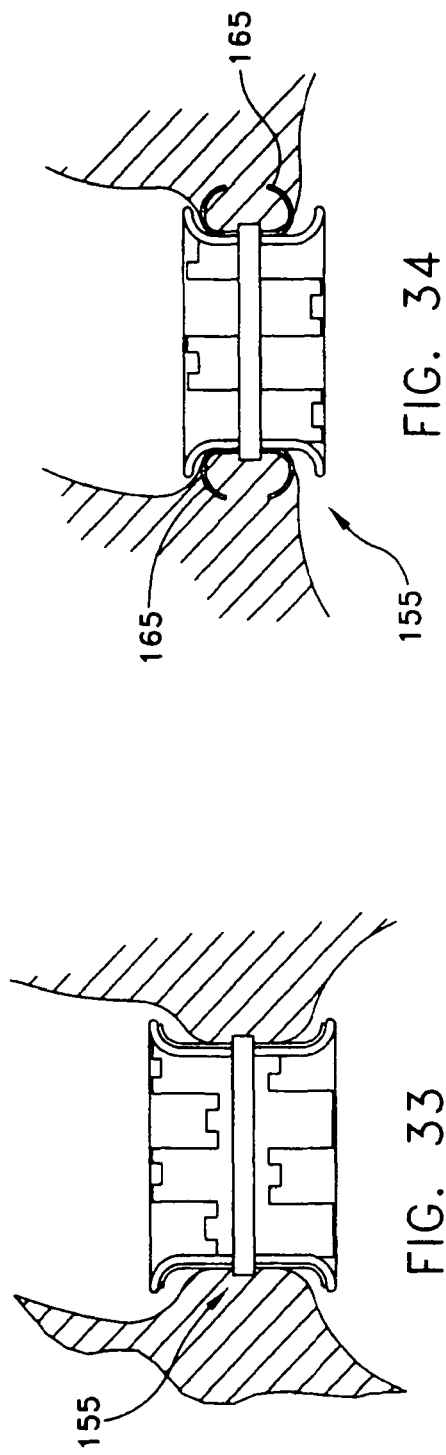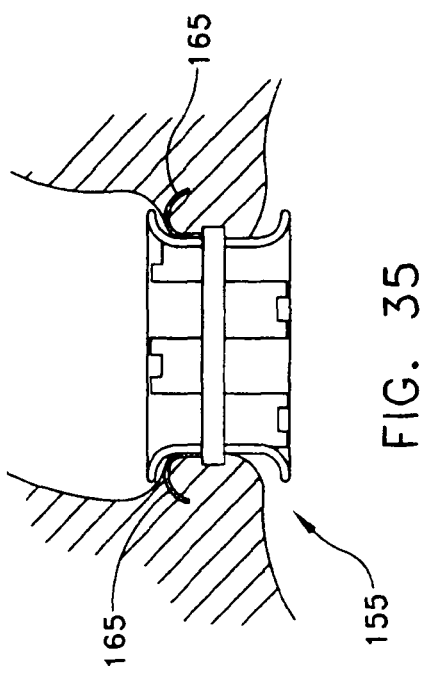

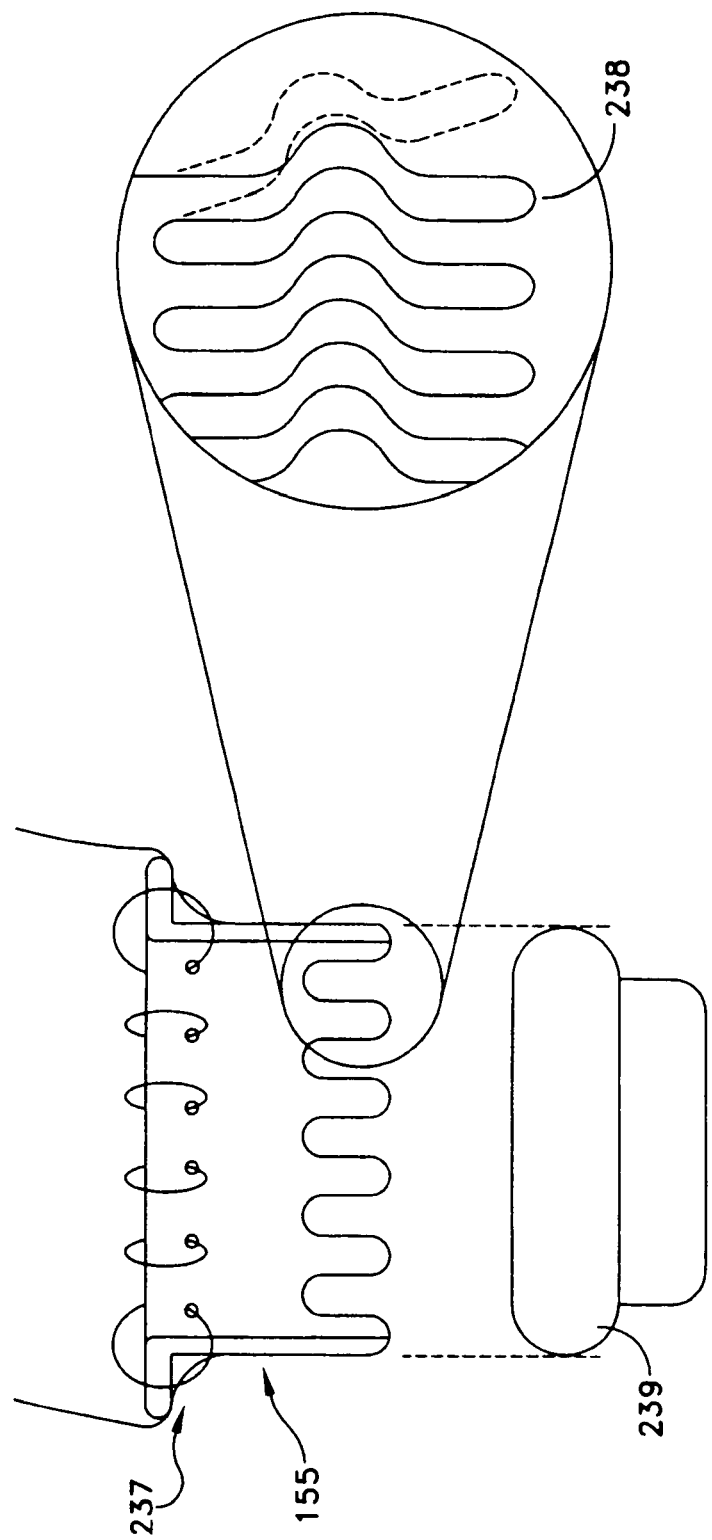

FIXATION BAND FOR AFFIXING A PROSTHETIC HEART VALVE TO TISSUE

REFERENCE TO PENDING PRIOR PATENT APPLICATIONS

This application is a Continuation of pending U.S. application Ser. No. 12/587,041, filed Oct. 1, 2009, which is a Divisional of U.S. application Ser. No. 11/479,357, filed Jun. 29, 2006, now U.S. Pat. No. 7,611,535, which is a Divisional of U.S. application Ser. No. 10/414,766, filed Apr. 16, 2003, now U.S. Pat. No. 7,097,659, which: 1) is a Continuation-In-Part of U.S. application Ser. No. 09/949,061, filed Sep. 7, 2001, now U.S. Pat. No. 6,846,325; and 2) which claims the benefit of U.S. Provisional Application No. 60/373,059, filed Apr. 16, 2002, the entire disclosures of which are hereby incorporated by reference.

FIELD OF THE INVENTION

This invention relates to surgical apparatus in general, and more particularly to prosthetic heart valves.

BACKGROUND OF THE INVENTION

The human heart consists of four chambers: the right atrium for receiving blood from systemic circulation; the right ventricle for receiving blood from the right atrium and pumping it to the lungs; the left atrium for receiving oxygenated blood from the lungs; and the left ventricle for receiving oxygenated blood from the left atrium and pumping it to systemic circulation.

The human heart also consists of four valves: the tricuspid valve located between the right atrium and the right ventricle; the pulmonary valve located at the output of the right ventricle; the mitral valve located between the left atrium and the left ventricle; and the aortic valve located at the output of the left ventricle.

In some circumstances (e.g., a birth defect, disease, etc.) a natural heart valve may need to be replaced by a prosthetic heart valve. In this situation, sometimes referred to as "on pump" surgery, the patient must, be placed on a heart-lung machine and the heart stopped while the defective heart valve is removed and the prosthetic heart valve installed through a major incision made in the wall of the heart. The prosthetic heart valve is typically sutured in place at the annulus, or seat, of the natural heart valve using a sewing cuff disposed about the circular periphery of the prosthetic heart valve.

While such surgery is typically successful, it is also highly traumatic to the body and the use of the heart-lung machine may raise issues of subtle mental impairment in the near term following surgery.

In view of the trauma associated with a major heart wall incision and possible subtle mental impairment which may be associated with the use of a heart-lung machine, it has been proposed to effect valve replacement without placing the patient on a heart-lung machine and stopping the heart. See, for example, PCT Patent Application No. PCT/US00/02126, filed Jan. 27, 2000 by Gregory Lambrecht et al. for CARDIAC VALVE PROCEDURE METHODS AND DEVICES, published Aug. 3, 2000 as PCT Patent Publication No. WO 00/44313. This type of surgery is sometimes referred to as "off-pump", or "beating heart", surgery.

It has been recognized that if a heart valve is to be replaced with "off-pump", "beating heart" surgery, the incisions made into the vascular system should be as small as possible. However, this can make it difficult to secure the prosthetic heart valve in place, since the prosthetic heart valve is typically sutured to the annulus, or seat, of the natural heart valve, and since suturing (including knot tying) can be difficult to effect through small incisions. This can be particularly true where the incisions may be made into the vascular system at a location remote from the valve seat, e.g., in the superior vena cava in the case of the tricuspid valve, or in the pulmonary artery in the case of the pulmonary valve, or the pulmonary veins in the case of the mitral valve, or the aorta in the case of the aortic valve.

SUMMARY OF THE INVENTION

As a result, one object of the present invention is to provide novel apparatus for quickly, easily and conveniently affixing a prosthetic heart valve in position within the heart.

Another object of the present invention is to provide a novel fixation band for affixing a prosthetic heart valve in position within the heart.

And another object of the present invention is to provide a novel method for affixing a prosthetic heart valve in position within the heart.

These and other objects of the present invention are addressed by the provision and use of a novel fixation band for affixing a prosthetic heart valve in position within the heart.

In one preferred form of the invention, the fixation band generally comprises a tubular frame having a distal end and a proximal end, and a tube having a distal end and a proximal end. The tubular frame comprises a plurality of longitudinally-extending members each having a hook on its distal end and fixation means on its proximal end. The tubular frame also comprises at least one laterally-extending member for stabilizing the longitudinally-extending members relative to one another so as to form the complete tubular frame. The tube is positioned inside the longitudinally-extending members, with the distal end of the tube being everted back over the aforementioned hooks. A sewing cuff is formed in the tube distal to the distalmost end of the longitudinally-extending members.

In use, a standard prosthetic valve is secured to the distal end of the fixation band by suturing the prosthetic valve's sewing cuff to the fixation band's sewing cuff. Next, the prosthetic valve, with fixation band attached, is advanced to the valve's seat. Then the fixation band's tubular frame is pulled proximally slightly. This action causes the ends of the hooks to pass through the side wall of the everted tube and into the surrounding tissue at the valve's seat, whereby the fixation band, and hence the prosthetic valve, will be fixed against further proximal movement. Next, the fixation band's fixation means are deployed so as to secure the proximal end of the fixation band to the surrounding tissue, whereby the fixation band, and hence the prosthetic valve, will be fixed against distal movement.

In one form of the invention, the fixation means may be deployed by bending them radially outwardly so that they engage the surrounding tissue.

In another form of the present invention, the fixation means may be deployed by removing a restraining device, whereby the fixation means will automatically deploy against the surrounding tissue.

In another form of the present invention, there is provided a fixation band for affixing a prosthetic heart valve to tissue, the fixation band comprising: a structure having a proximal end and a distal end in opposition to one another, and a lateral region between the proximal end and the distal end, wherein the prosthetic heart valve is attached to one of the proximal end and the distal end of the structure; a plurality of barbs selectively configurable between a first position and a second position, the barbs being contained within a peripheral boundary of the lateral region of the structure in the first position, and the barbs being extended from the peripheral boundary of the lateral region of the structure in the second position; and an actuator for selectively moving the plurality of barbs between the first position and the second position.

In another form of the present invention, there is provided a prosthetic heart valve assembly comprising: a prosthetic heart valve comprising a frame, at least one leaflet adapted to open and close relative to the frame; and a fixation band for affixing the prosthetic heart valve to tissue, the fixation band comprising: a structure having a proximal end and a distal end in opposition to one another, and a lateral region between the proximal end and the distal end, wherein the prosthetic heart valve is attached to one of the proximal end and the distal end of the structure; a plurality of barbs selectively configurable between a first position and a second position, the barbs being contained within a peripheral boundary of the lateral region of the structure in the first position, and the barbs being extended from the peripheral boundary of the lateral region of the structure in the second position; and an actuator for selectively moving the plurality of barbs between the first position and the second position.

In another form of the present invention, there is provided a method for affixing a prosthetic heart valve to tissue, the method comprising: providing a fixation band for affixing a prosthetic heart valve to tissue, the fixation band comprising: a structure having a proximal end and a distal end in opposition to one another, and a lateral region between the proximal end and the distal end, wherein the prosthetic heart valve is attached to one of the proximal end and the distal end of the structure; a plurality of barbs selectively configurable between a first position and a second position, the barbs being contained within a peripheral boundary of the lateral region of the structure in the first position, and the barbs being extended from the peripheral boundary of the lateral region of the structure in the second position; and an actuator for selectively moving the plurality of barbs between the first position and the second position; positioning the fixation band adjacent to the tissue; and actuating the fixation band so as to affix the prosthetic valve to tissue.

In another form of the present invention, there is provided a method for affixing a prosthetic heart valve to tissue, the method comprising: positioning a fixation band adjacent to the tissue; and removing a pin in engagement with a spring in a loaded configuration so as to release the spring, cause a cog to rotate, and deploy barbs through a lateral portion of the fixation band into the tissue surrounding the fixation band.

In another form of the present invention, there is provided a fixation band for affixing a prosthetic heart valve to tissue, the fixation band comprising: a proximal annular portion and a distal annular portion selectively positioned relatively to one another, the proximal annular portion and the distal annular portion each having a proximal side and a distal side, the proximal side of the distal annular portion and the distal side of the proximal annular portion being oriented toward one another, and the prosthetic heart valve being attached to one of the distal side of the distal annular portion and the proximal side of the proximal annular portion; a plurality of staples configured between the distal side of the proximal annular portion and the proximal side of the distal annular portion; and a compression device in attachment to the proximal annular portion and the distal annular portion, the compression device being configured to selectively position the proximal annular member and the distal annular member toward one another so as to compress the plurality of staples therebetween and deploy the plurality of staples into tissue so as to affix the prosthetic heart valve to the tissue.

In another form of the present invention, there is provided a prosthetic heart valve assembly comprising: a prosthetic heart valve comprising a frame, and at least one leaflet adapted to open and close relative to the frame; and a fixation band for affixing a prosthetic heart valve to tissue, the fixation band comprising: a proximal annular portion and a distal annular portion selectively positioned relatively to one another, the proximal annular portion and the distal annular portion each having a proximal side and a distal side, the proximal side of the distal annular portion and the distal side of the proximal annular portion being oriented toward one another, and the prosthetic heart valve being attached to one of the distal side of the distal annular portion and the proximal side of the proximal annular portion; a plurality of staples configured between the distal side of the proximal annular portion and the proximal side of the distal annular portion; and a compression device in attachment to the proximal annular portion and the distal annular portion, the compression device being configured to selectively position the proximal annular member and the distal annular member toward one another so as to compress the plurality of staples therebetween and deploy the plurality of staples into tissue so as to affix the prosthetic heart valve to the tissue.

In another form of the present invention, there is provided a method for affixing a prosthetic heart valve to tissue, the method comprising: providing a fixation band for affixing a prosthetic heart valve to tissue, the fixation band comprising: a proximal annular portion and a distal annular portion selectively positioned relatively to one another, the proximal annular portion and the distal annular portion each having a proximal side and a distal side, the proximal side of the distal annular portion and the distal side of the proximal annular portion being oriented toward one another, and the prosthetic heart valve being attached to one of the distal side of the distal annular portion and the proximal side of the proximal annular portion; a plurality of staples configured between the distal side of the proximal annular portion and the proximal side of the distal annular portion; and a compression device in attachment to the proximal annular portion and the distal annular portion, the compression device being configured to selectively position the proximal annular member and the distal annular member toward one another so as to compress the plurality of staples therebetween and deploy the plurality of staples into tissue so as to affix the prosthetic heart valve to the tissue; positioning the fixation band adjacent to the tissue; and actuating the compression device so as to move the proximal annular portion and the distal annular portion toward one another so as to deploy the plurality of staples into the tissue.

In another form of the present invention, there is provided a method for affixing a prosthetic heart valve to tissue, the method comprising: positioning a fixation band having the prosthetic heart valve attached thereto adjacent to the tissue; and actuating a compression device attached to the fixation band so as to move a proximal annular portion and a distal annular portion of the fixation band toward one another so as to deploy a plurality of staples into the tissue.

In another form of the present invention, there is provided a method for affixing a prosthetic heart valve to tissue, the method comprising: positioning a fixation band adjacent to tissue; actuating a compression device attached to the fixation band to move a proximal annular portion and a distal annular portion of the fixation band toward one another so as to deploy a plurality of staples into the tissue; and attaching the prosthetic heart valve to the fixation band.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 9A-12B are schematic views showing a fixation apparatus having side deploying barbs;

FIGS. 33-35 are schematic views showing fixation of an prosthetic aortic heart valve at an annulus of the native aortic valve;

FIGS. 36-39 are schematic views showing fixation of an prosthetic heart valve using snap fit means.

DETAILED DESCRIPTION OF THE PREFERRED EMBODIMENTS

Figure 1:
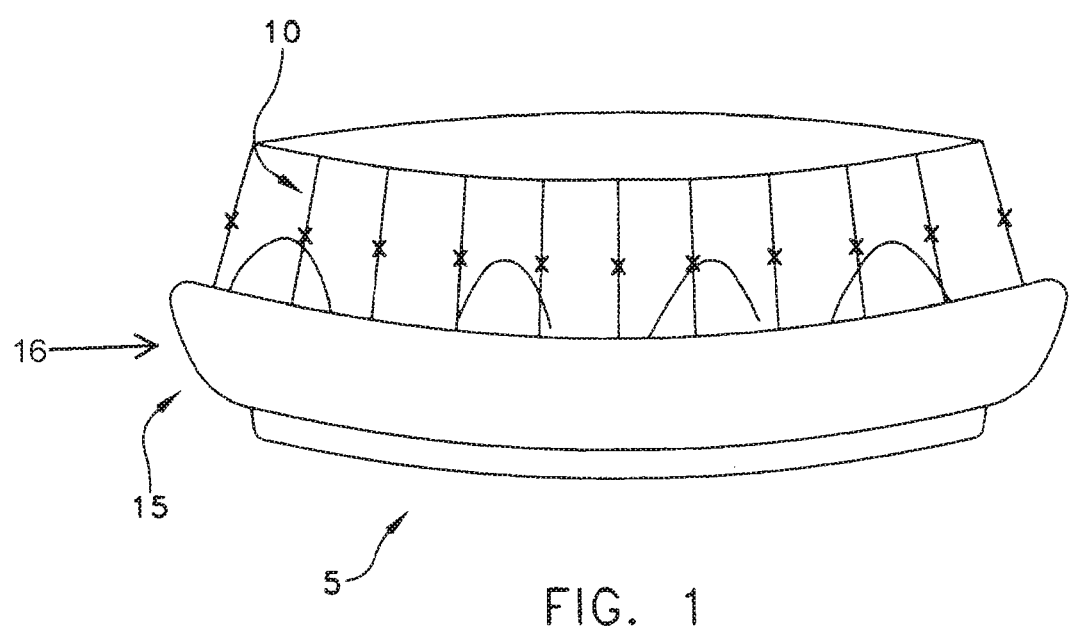
FIG. 1 is a schematic view of a fixation band formed in accordance with the present invention.

Looking first at FIG. 1, there is shown a fixation band 5 which comprises one preferred form of the invention. Fixation band 5 generally comprises a tubular frame 10 and a tube 15.

Figure 2:
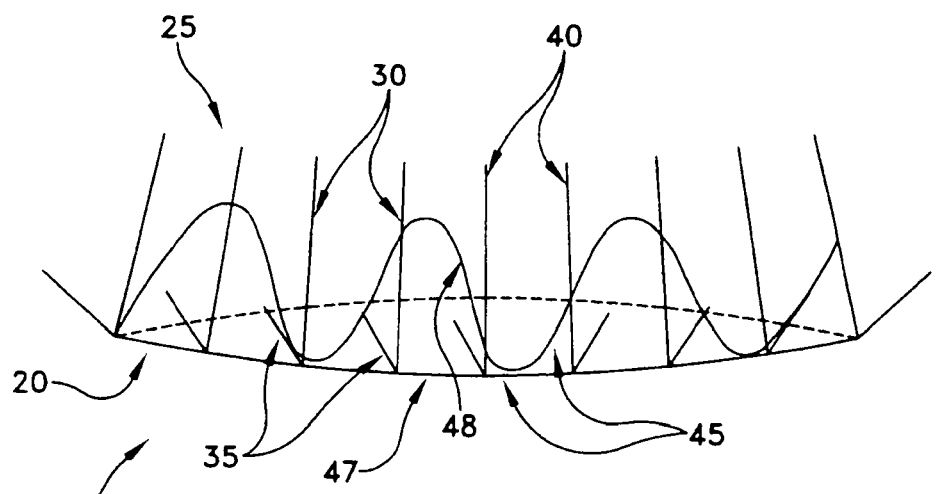
FIG. 2 is a schematic view of the fixation band's tubular frame.

Tubular frame 10 is shown in greater detail in FIG. 2. Tubular frame 10 generally comprises a distal end 20 and a proximal end 25. Tubular frame 10 comprises a plurality of longitudinally-extending members 30 each having a hook 35 on its distal end, and fixation means 40 (discussed in further detail below) on its proximal end. Tubular frame 10 also comprises at least one laterally-extending member 45 for stabilizing the longitudinally-extending members 30 relative to one another so as to form the complete tubular frame. In one form of the invention, each laterally-extending member 45 extends completely around the circumference of the frame, in the manner shown in FIG. 2. Alternatively, a series of separate laterally-extending members 45 may be used to span the circumference of tubular frame 10. Furthermore, in one form of the invention, laterally-extending member 45 may be in the form of a circular hoop, like the hoop of a barrel, such as the laterally-extending member 47 shown in FIG. 2. Alternatively, and/or in addition, laterally-extending member 45 may have a serpentine configuration, such as the laterally-extending member 48 shown in FIG. 2.

Figure 3:
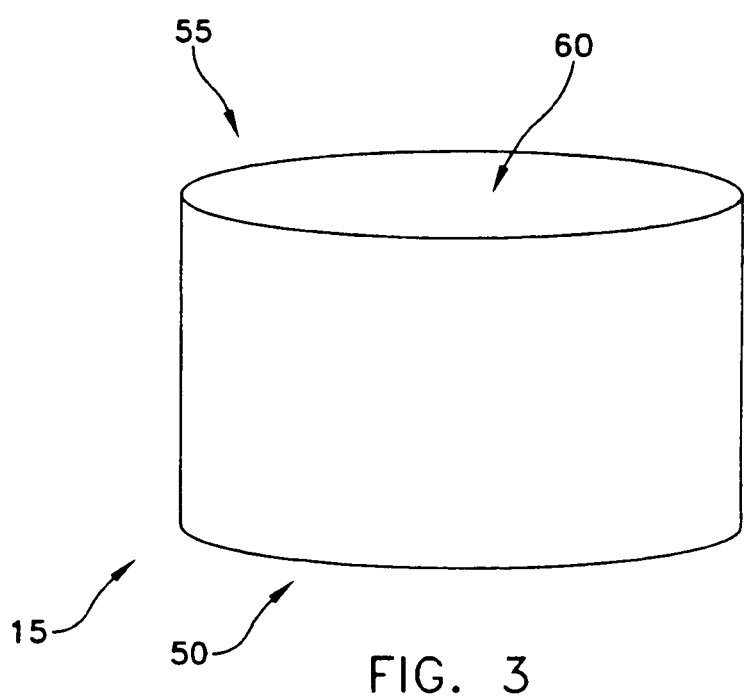
FIG. 3 is a schematic view of the fixation band's tube prior its assembly with the tubular frame.

Tube 15 is, initially, an ordinary straight tube such as is shown in FIG. 3, i.e., it is a hollow structure having a distal end 50, a proximal end 55 and a central lumen 60 extending therebetween. Tube 15 is preferably formed out of material which is easily incorporated in tissue, e.g., Dacron polyester or the like. Tube 15 may be vertically pleated or elastic, whereby to allow the material to stretch radially.

Figure 4:
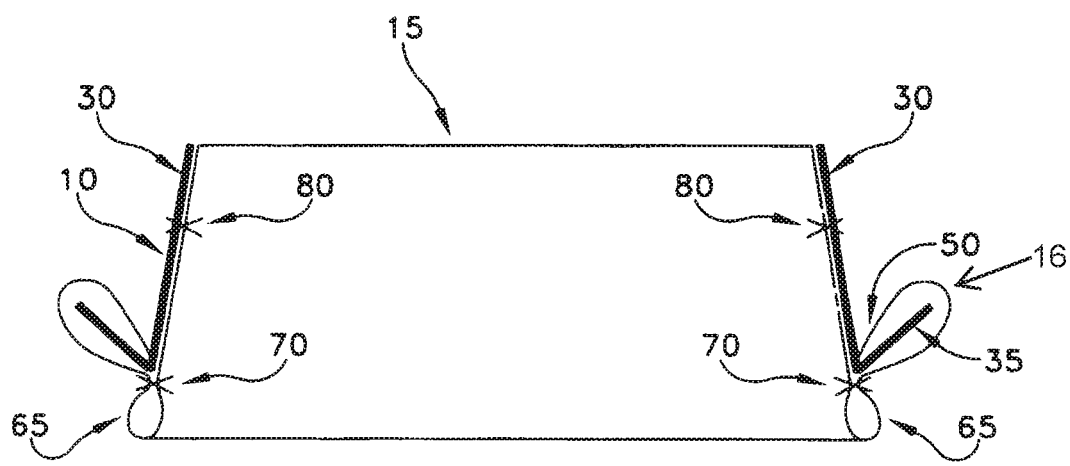
FIG. 4 is a schematic view of the complete fixation band shown in FIG. 1.

Tube 15 is preferably mounted to tubular frame 10 as follows. First, the distal end 50 of tube 15 is passed, distally, down the interior of tubular frame 10. Then the distal end 50 of tube 15 is everted (FIG. 4) so as to fold it back over, and cover, the hooks 35 of longitudinally-extending members 30.

As this is done, a sewing cuff 65 is formed in tube 15 distal to the distalmost end of longitudinally-extending members 30. Tube 15 may then be secured in this position, e.g., with sutures 70 maintaining sewing cuff 65 and with sutures 80 holding tube 15 to longitudinally-extending members 30.

Figure 5:
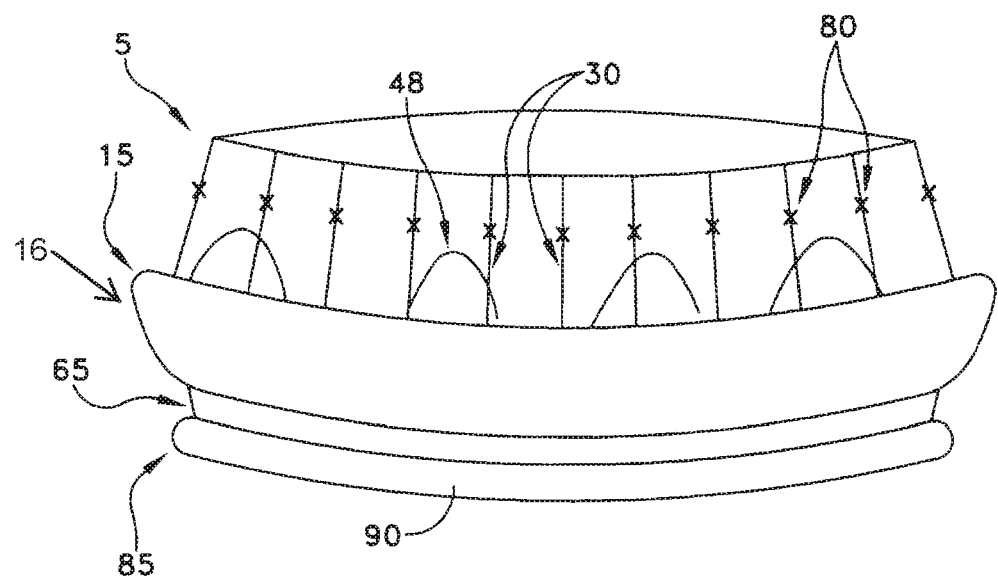
FIG. 5 is a schematic view showing a prosthetic heart valve secured to the fixation band of FIG. 1.
Figure 6:
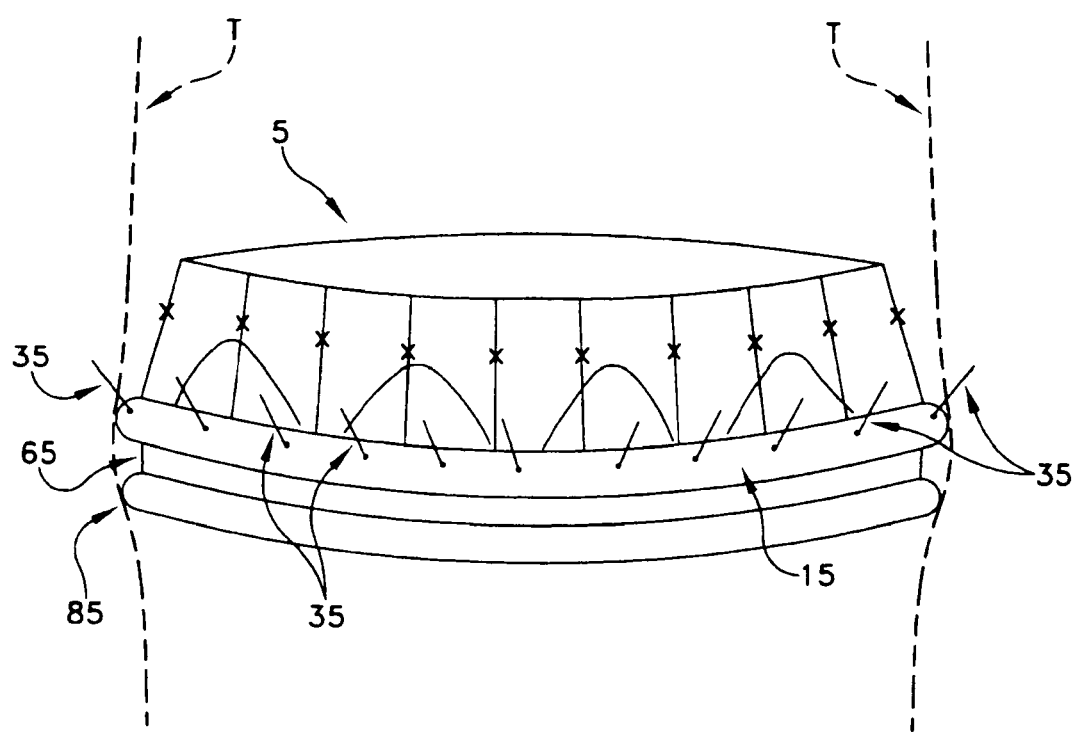
FIG. 6 is a schematic view showing the assembly of FIG. 5 after deployment of the fixation band's distal hooks.
Figure 7:
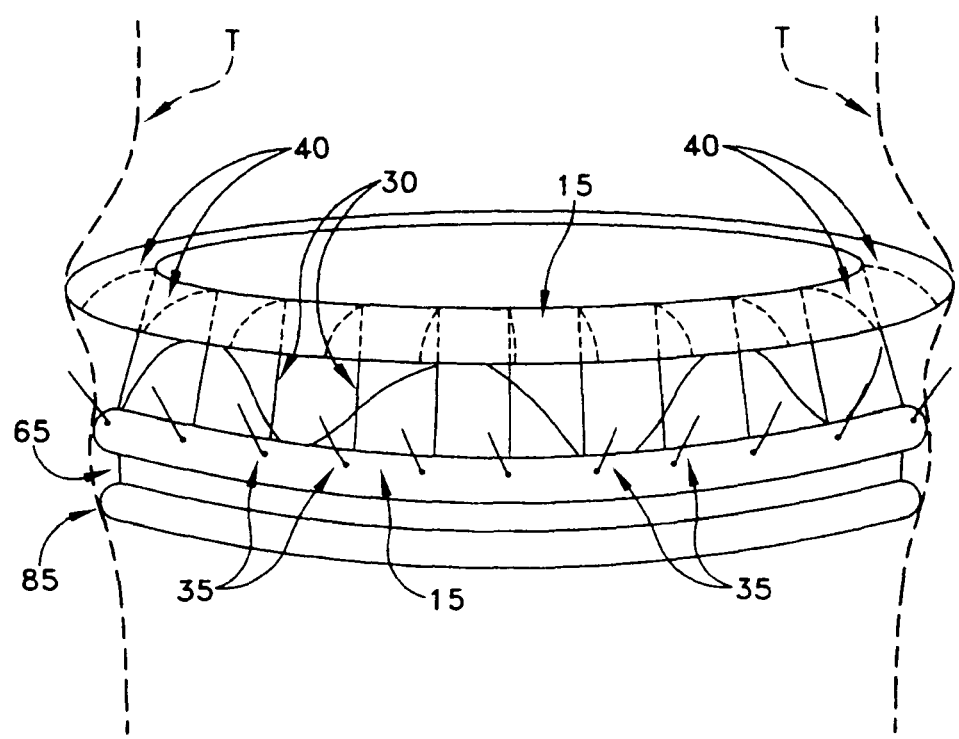
FIG. 7 is a schematic view showing the assembly of FIG. 6 after deployment of the fixation band's proximal fixation means.

In use, a standard prosthetic heart valve 85 (FIG. 5) is secured to the distal end of fixation band 5 by sewing the prosthetic heart valve's sewing cuff 90 to the fixation band's sewing cuff 65. Next, the prosthetic valve 85, with fixation band 5 attached, is advanced to the valve's seat. Then the fixation band's tubular frame 10 is pulled proximally slightly. This action causes the ends of the hooks 35 to pass through the side wall of the everted tube 15 (FIG. 6) and into the surrounding tissue T at the valve's seat, whereby fixation band 5, and hence prosthetic valve 85, will be fixed against further proximal movement. Next, the fixation band's fixation means 40 are deployed (FIG. 7) so as to secure the proximal end of the fixation band to surrounding tissue, whereby the fixation band, and hence the prosthetic valve, will be fixed against distal movement. Where the fixation means 40 are secured to the proximal end of tube 15, the proximal end of tube 15 will follow the curvature of the deploying fixation means 40, such as is shown in FIG. 7. Alternatively, if fixation means 40 are free to move independently outboard relative to the proximal end of tube 40, either because they are not secured to tube 15 or they extend past the proximal end of the tube, fixation means 40 are free to move separately into the surrounding tissue.

In one form of the invention, fixation means 40 may be deployed by bending the proximal ends of longitudinally-extending members 30 outwardly, e.g., with an annular forming tool or a forceps-type device.

Figure 8:
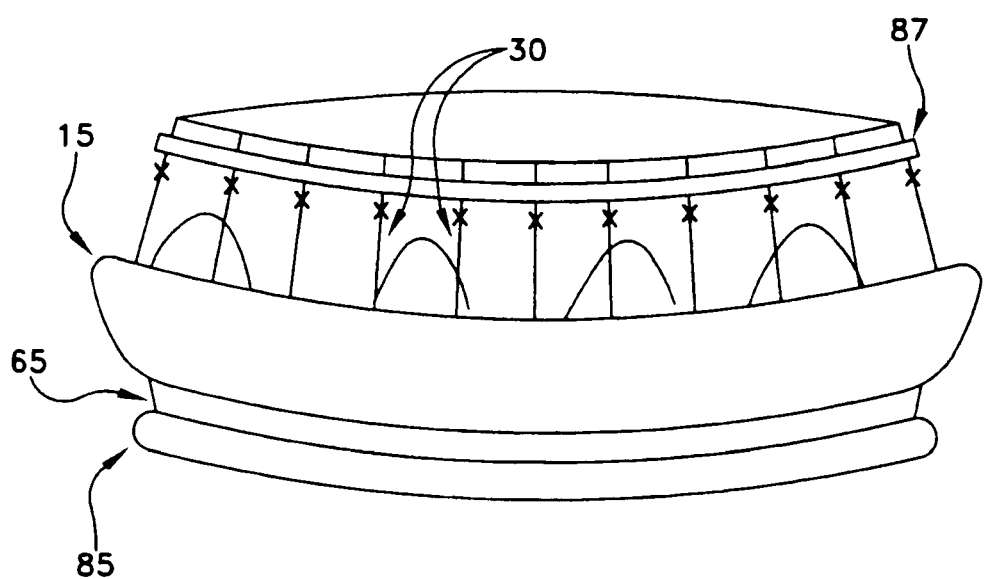
FIG. 8 is a schematic view showing a restraining device for restraining the fixation band's proximal fixation mean.
Figure 10B:
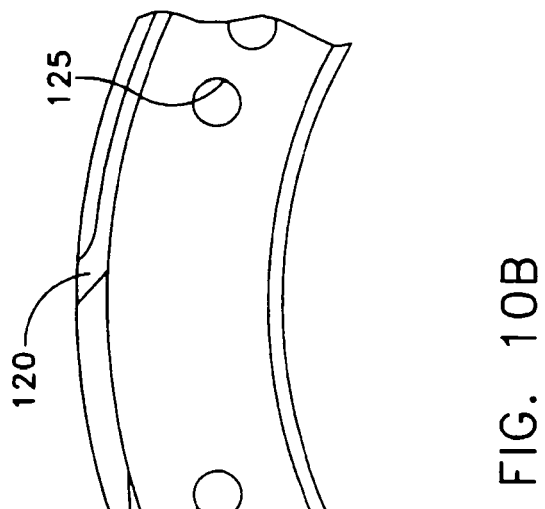
Figure 10A:
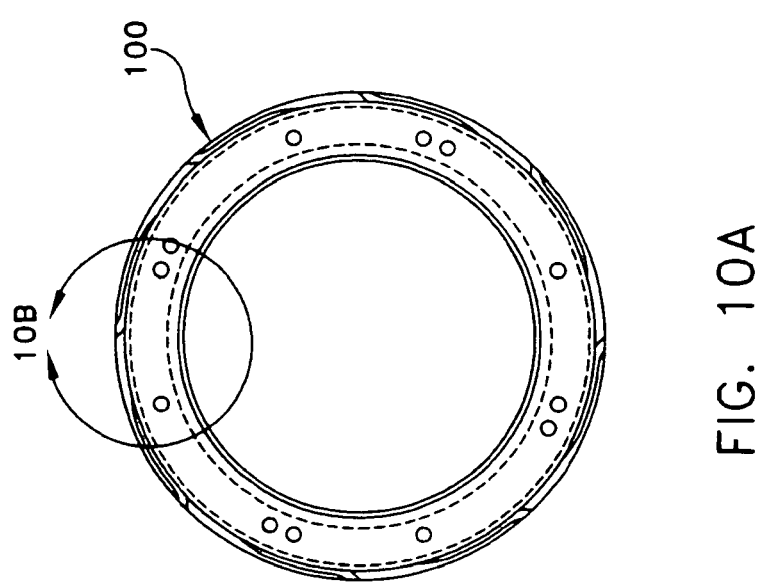

In another form of the invention, fixation means 40 may be deployed by removing a restraining device, e.g., a collar 87 (FIG. 8), whereby fixation means 40 will automatically deploy against the surrounding tissue.

Fixation band 5 may be used to affix prosthetic heart valve 85 to tissue in a conventional on-pump surgical procedure. Alternatively, and more preferably, fixation band 5 may be used to affix prosthetic heart valve 85 to tissue in a beating heart, off-pump surgical procedure. In this case, the assembled heart valve 85 and fixation band 5 are advanced to the intended valve seat by passing the assembly through an appropriate vascular pathway, e.g., in the case of the aortic valve, by passing the assembly down the aorta.

It should be appreciated that various modifications may be made to the preferred embodiments described above without departing from the scope of the present invention. Thus, for example, in the foregoing description, tubular frame 10 is described as being fully assembled (i.e., laterally-extending member 45 is secured to longitudinally-extending member 30) prior to being joined with tube 15 so as to form the complete fixation band 5. However, it should also be appreciated that longitudinally-extending members 30 and/or the laterally-extending member 45 may be secured to tube 15 prior to being joined to one another.

Furthermore, in the foregoing description, tube 15 is describe as being, prior to eversion, an ordinary straight tube. However, if desired, tube could be flared outwardly toward its distal end 50 to facilities eversion over hooks 35, and/or it could include a radially-extending flange 16 at its distal end to facilitate eversion over hooks 35, where the flange 16 may be formed separately from the main body of the tube.

Referring next to FIGS. 9A-13D, there is shown a side deploying apparatus 90 for affixing an prosthetic aortic heart valve 95 in position inside the aorta. Side deploying apparatus 90 is a multi-state device that can be safely guided into the aorta, properly positioned near the annulus of the native aortic valve, and then, by either automatic action or operator control, be deployed by means of introducing a number of barbs 100 into the aortic valve annulus. Side deploying apparatus 90 may also have the capability of its barbs 100 being retracted for either better positioning or removal.

Looking now at FIGS. 9A-9D, in a preferred embodiment of the present invention, apparatus 90 comprises two shell portions 105 and two cog portions 110. In FIG. 9A, apparatus 90 is shown assembled and its barbs 100 deployed. In FIG. 9B, apparatus 90 is shown assembled, attached to a prosthetic valve 95 and its barbs 100 deployed, which keeps prosthetic valve 95 stationary relative to the wall of the aorta. Three significant features of shell 105 are: studs 115, which act as anchors for cog 110; the exit tracts 120, which allow for barbs 100 of cog 110 to exit shells 105; and the pinholes 125 through which actuating pins 130 (FIG. 11B) are inserted.

Figure 11B:
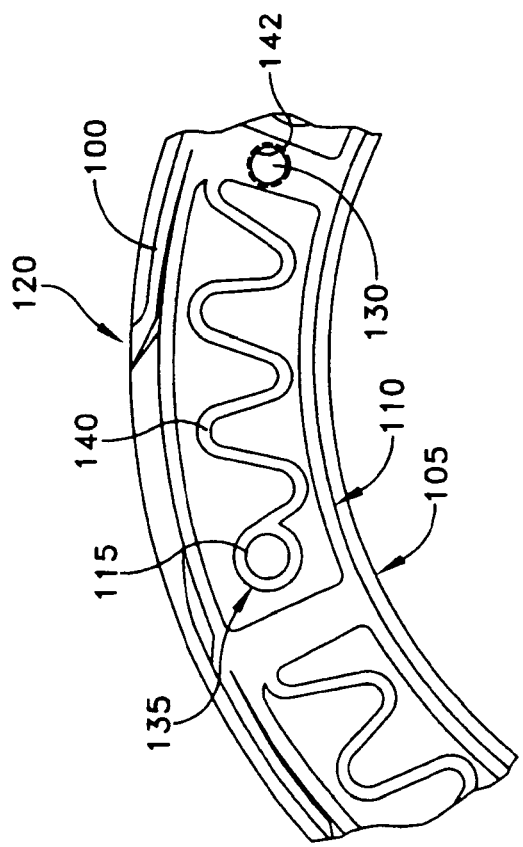
Figure 11A:
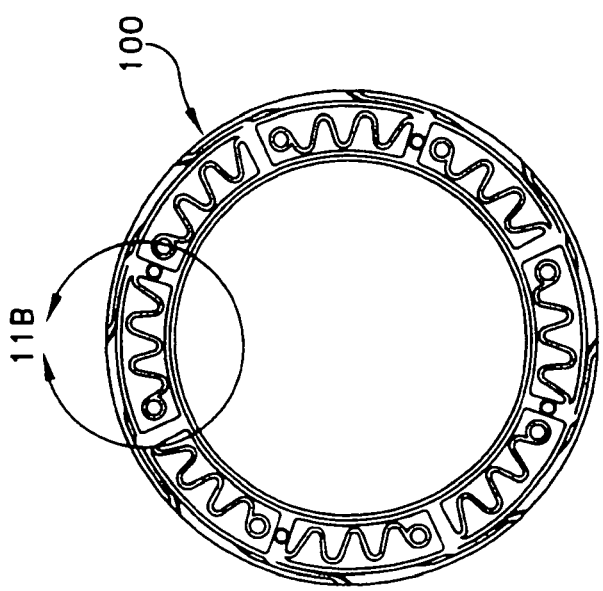

Looking now at FIGS. 11A and 11B, cog 110 is shown in a "loaded" form inside shell 105. Two cogs 110 are the moving parts of apparatus 90 and reside sandwiched next to each other inside shells 105, but in opposing directions to one another. Referring again to FIGS. 11A and 11B, cog 110 has several significant features integral to its function: eyelets 135, springs 140, barbs 100, and pinholes 142. When in the loaded state, springs 140 of cog 110 are stretched and barbs 100 are folded down while studs 115 on shell 105 protrude through eyelets 135 and pins 130 are inserted through pinholes 142 so as to maintain the position of each cog 110 relative to shell 105.

Figure 12B:
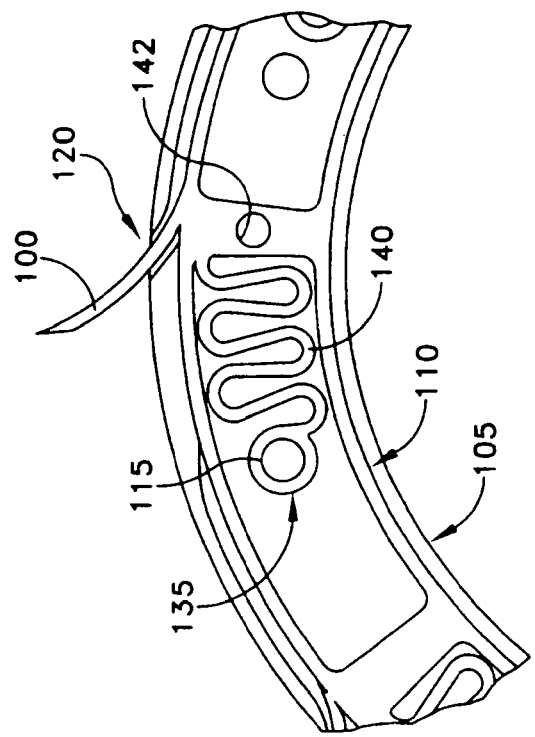
Figure 12A:
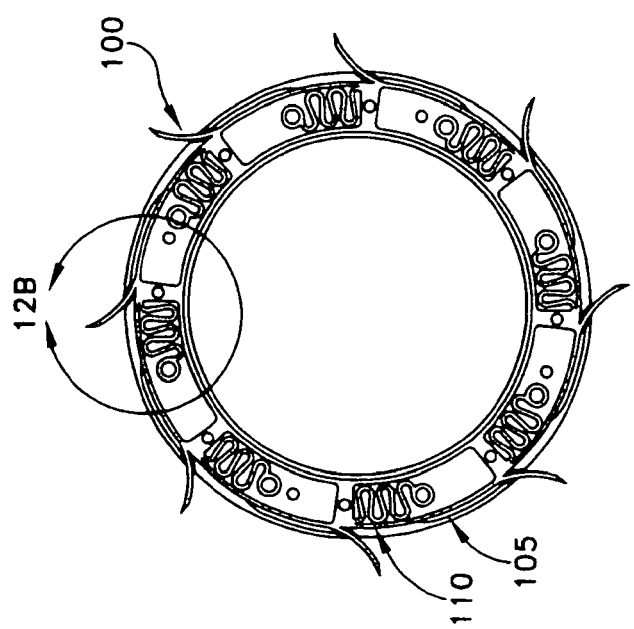

Looking now at FIGS. 12A and 12B, cog 110 is shown in the "deployed" form relative to shell 105. Here, barbs 100 are extended through exit tracts 120 and springs 140 are no longer stretched. Apparatus 90 can be transformed into the deployed state by removing pins 130 from pinholes 142 of each cog 110. When this happens, springs 140 each contract so as to rotate cog 110 relative to studs 115 of shell 105 and force barbs 100 out of exit tracks 120. To retract apparatus 90, force on pinholes 142 must be re-applied and cog 110 rotated back to its loaded position (see FIGS. 11A and 11B).

Figure 13B:
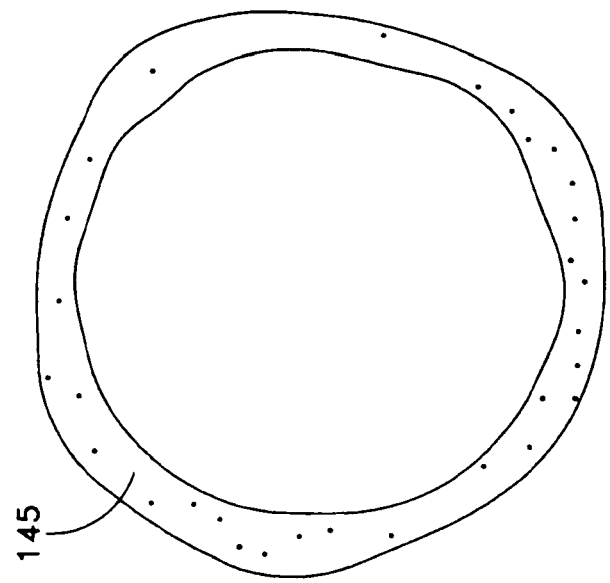
FIGS. 13A-13D are schematic views showing a heart valve replacement using the side deploying fixation apparatus shown in FIGS. 9A-12B.
Figure 13A:
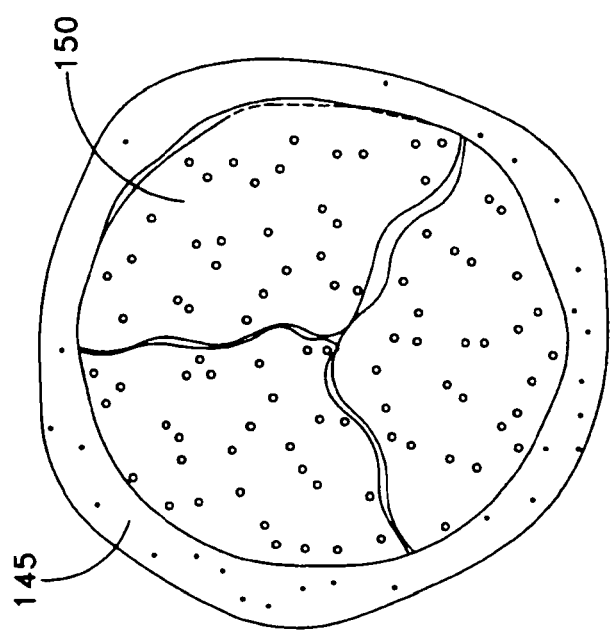
Figure 13D:
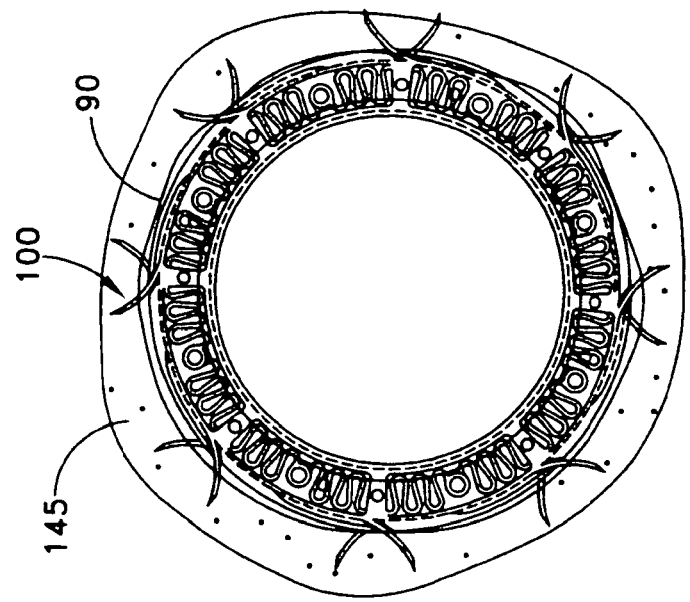
Figure 13C:
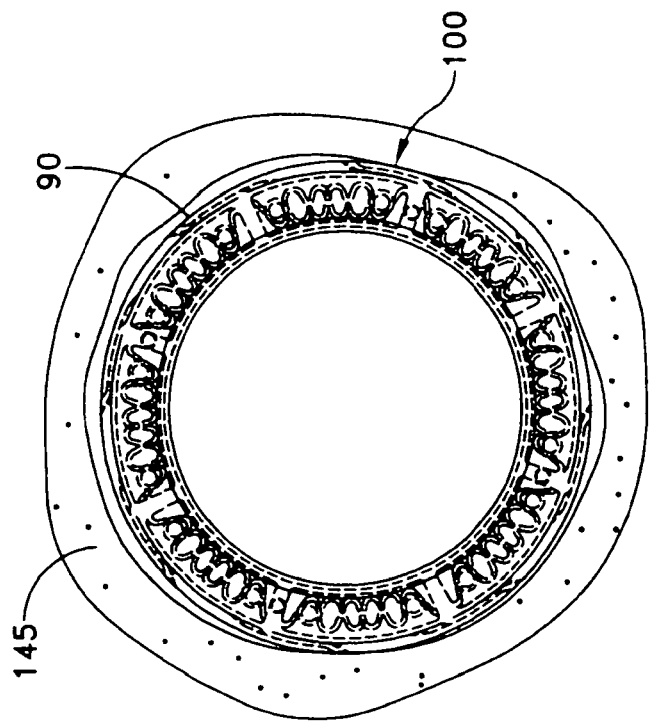

Looking next at FIGS. 13A-13D, there is shown an example of a typical heart valve replacement. In FIG. 13A, there is shown an aorta 145 with a native aortic valve 150. In FIG. 13B, aorta 145 is shown after valve 150 has been removed. In FIG. 13C, side deploying apparatus 90 is shown in an undeployed state (see FIGS. 11A and 11B) inside aorta 145. In FIG. 13D, side deploying apparatus 90 is shown in a deployed state (see FIGS. 12A and 12B) inside aorta 145.

In the preceding description, side deploying apparatus 90 is described in the context of affixing an prosthetic heart valve 95 in position within the aortic valve annulus. In this respect it should also be appreciated, however, that side deploying apparatus 90 may be used to affix some other heart valve within another cardiovascular structure.

Figure 14:
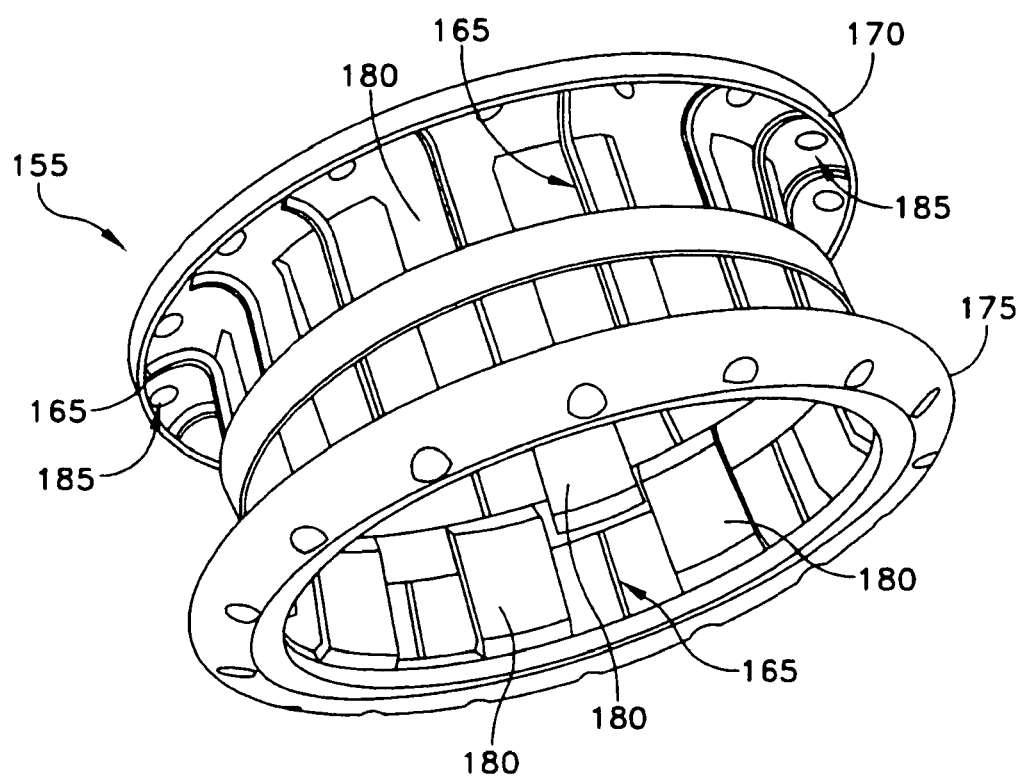
FIGS. 14-30 are schematic views showing fixation apparatus having compression deploying barbs.
Figure 15:
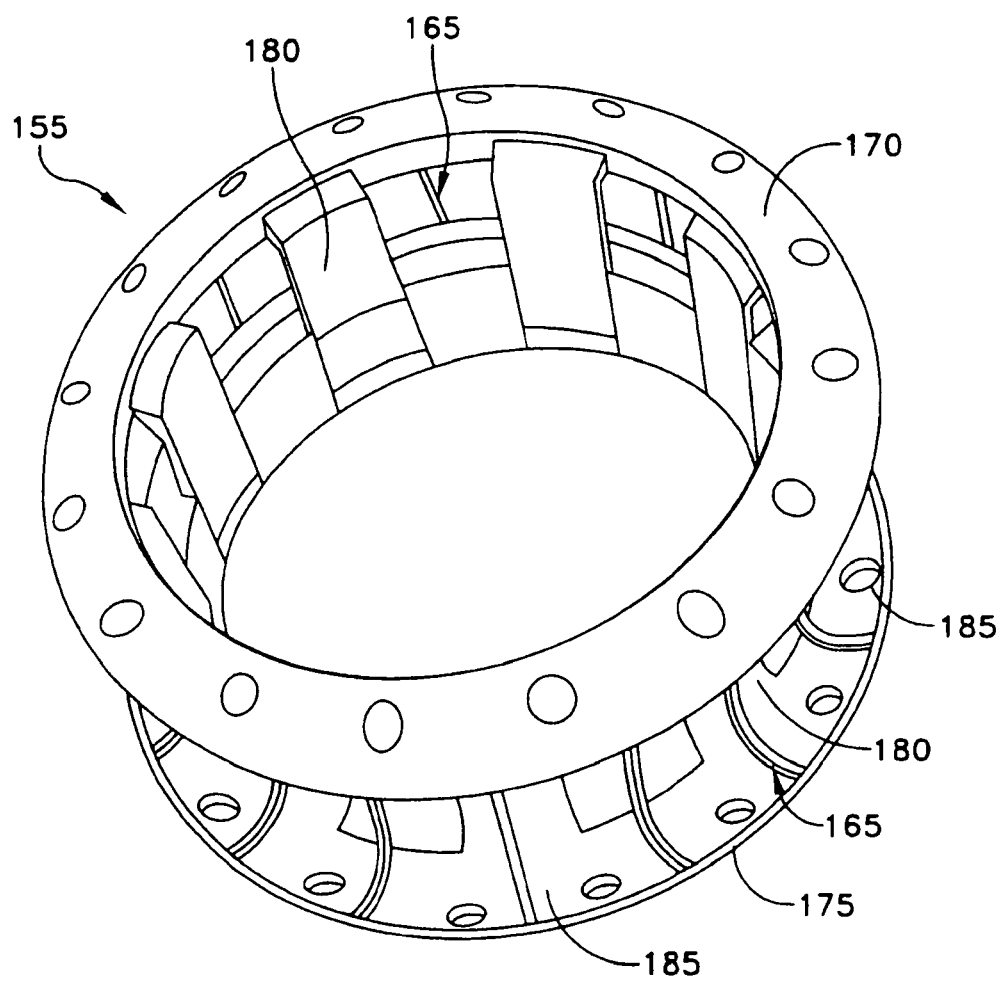
Figure 16:
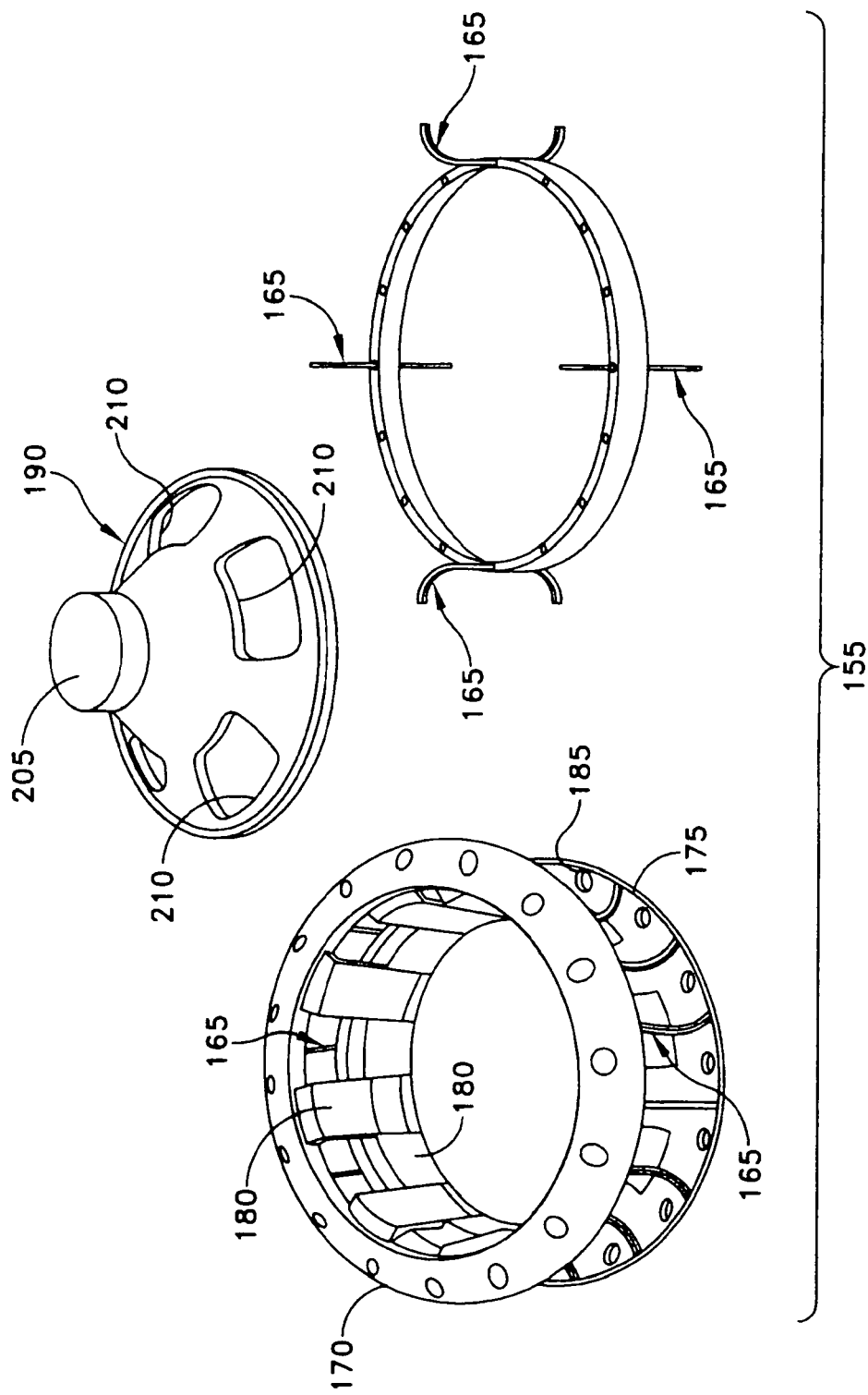

Referring now to FIGS. 14-40, there is shown an apparatus 155 (FIG. 14) for affixing an prosthetic aortic valve 160 (FIG. 17) in position inside the aortic valve annulus. Apparatus 155 is a compressive device that can be safely guided into the aorta, properly positioned near the annulus of the native aortic valve, and then, by either automatic action or operator control, deployed by means of advancing staples 165 (FIG. 17) into the aortic valve annulus. Compressive apparatus 155 may also have the capability of having its staples 165 retracted for either better positioning or removal of the apparatus. Compressive apparatus 155 may be positioned for fixation above, below, or at the annulus of the native aortic valve. Compressive apparatus 155 may also be positioned using an aortic approach or a left ventricular approach so as to advance it toward the annulus of the native aortic valve.

Looking now at FIGS. 14-22, in a preferred embodiment of the present invention, compressive apparatus 155 comprises a top ring 170 and a bottom ring 175 selectively positionable relative to one another by connector portions 180. Top ring 170 and bottom ring 175 each have a surface, forming an anvil 185, facing one another. In a preferred embodiment of the present invention, each anvil 185 (on top ring 170 and bottom ring 175) is shaped in an opening curve configuration so as to form a "C" shaped staple 165 (see FIG. 19) when deployed. In an alternative preferred embodiment of the present invention, each anvil 185 is shaped with a closing curve so as to form a "B" shaped staple (not shown) when deployed.

Looking next at FIGS. 17-22, in a preferred embodiment of the invention, apparatus 155 includes deployment means 190 for selectively actuating top ring 170 and bottom ring 175 relative to one another. Deployment means 190 generally comprise a handle 195, a plurality of cables 200 selectively connected to bottom ring 175 and extending to handle 195, and a support 205 selectively engaging top ring 170 and slidably connected to handle 200. In one preferred embodiment of the present invention, support 205 (see FIG. 16) comprises a solid component having passages 210 for blood flow formed therein. In another preferred embodiment of the invention, support 205 comprises three legs 215 (FIG. 17), which allow blood flow therebetween.

Now referring to FIGS. 17-22, in a preferred embodiment of the present invention, there is shown the compressive apparatus 155 and the prosthetic aortic heart valve 160 in connection to one another. Preferably, this connection is performed prior to implantation, either in an operating room by a physician or a manufacturing site by a manufacturer. In another preferred embodiment of the present invention, apparatus 155 and prosthetic aortic heart valve 160 are connected to one another in vivo, either prior to, or subsequent to, the fixation of apparatus 155 at or adjacent to an annulus of a native aortic heart valve (not shown).

Figure 17:
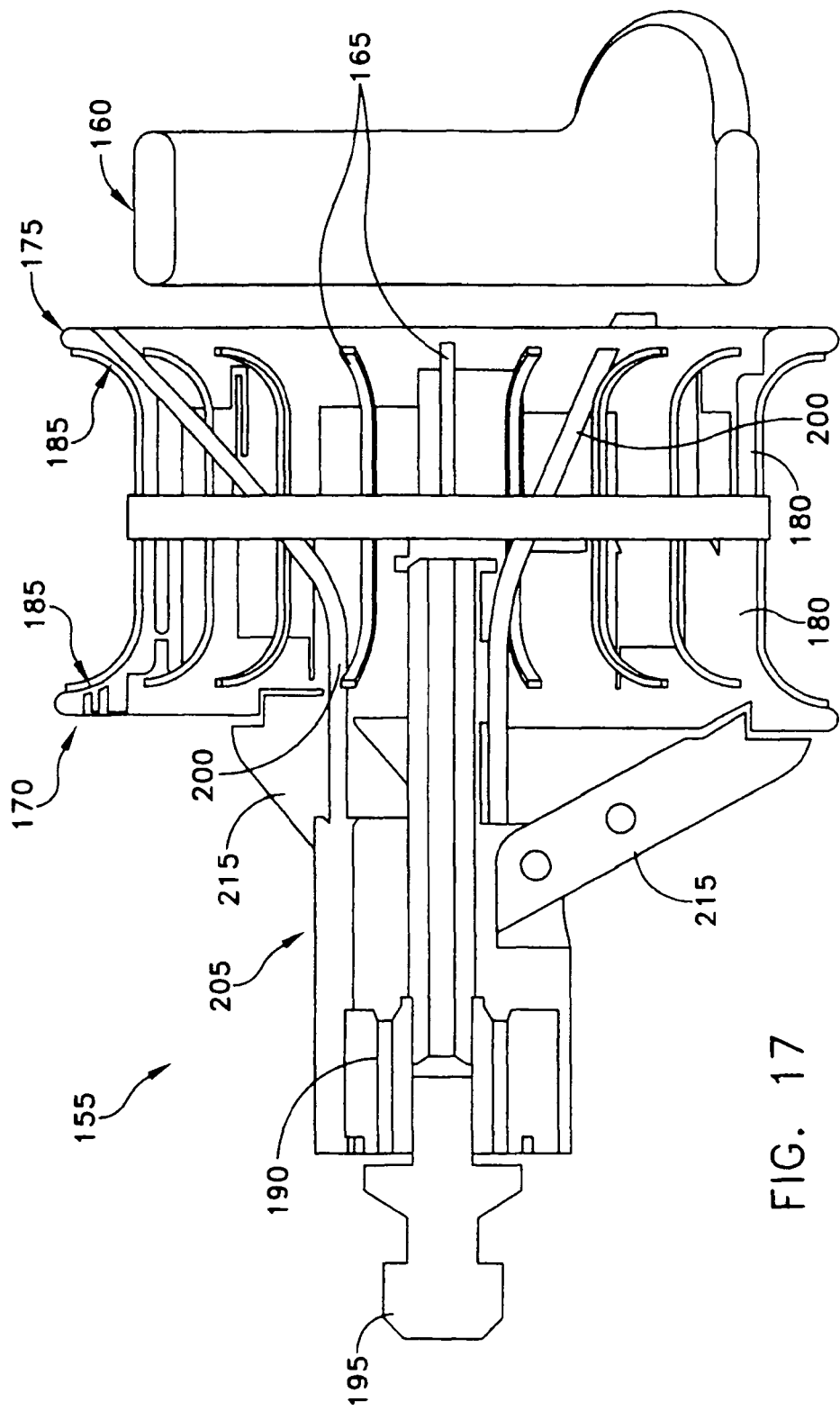
Figure 18:
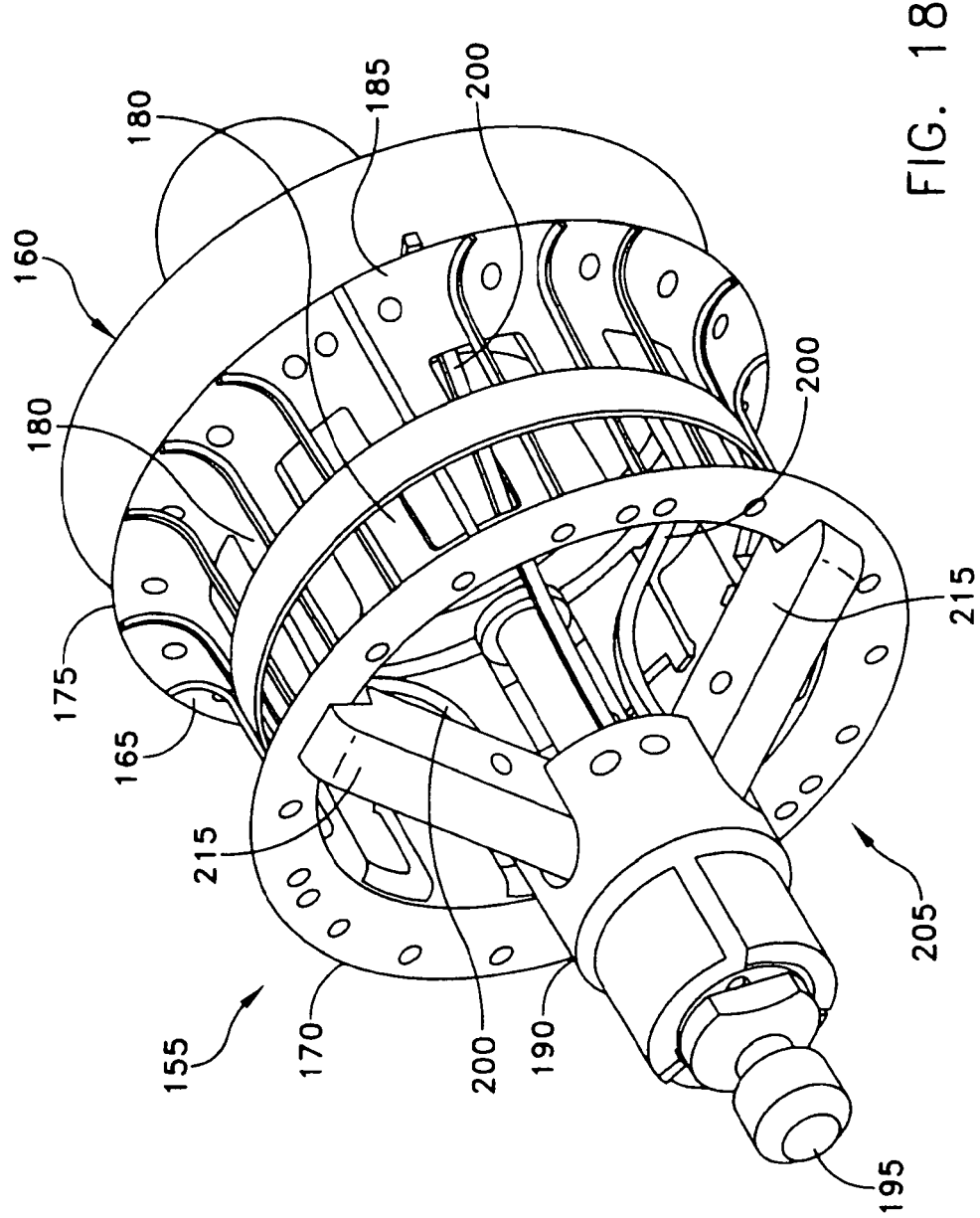

Looking next at FIGS. 17 and 18, apparatus 155 is shown prior to actuation, with top ring 170 and bottom ring 175 spaced apart from one another. While in this configuration, apparatus 155 is positioned at a desired deployment site, at or adjacent to the annulus of the native aortic valve (not shown).

Figure 19:
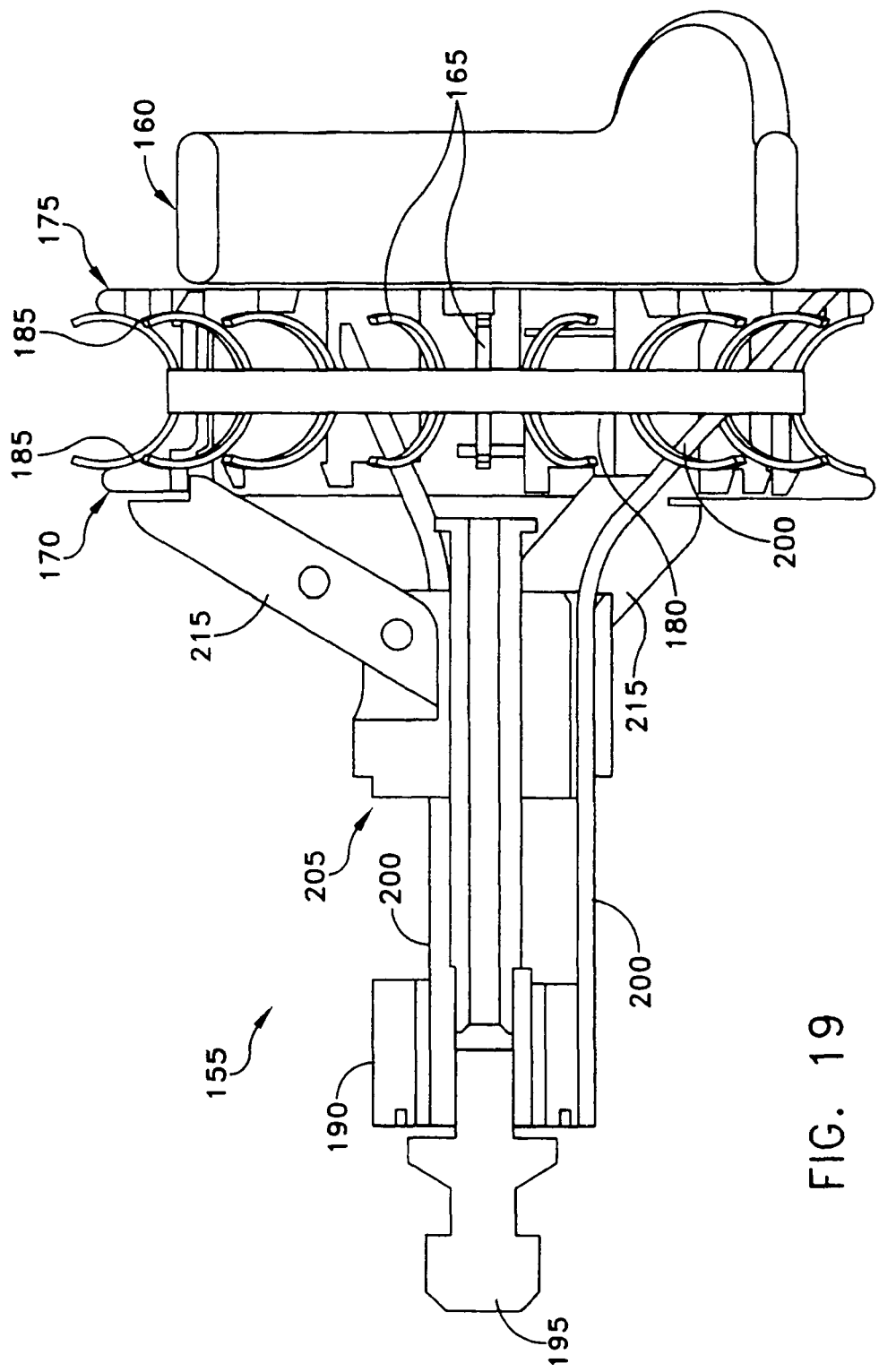
Figure 20:
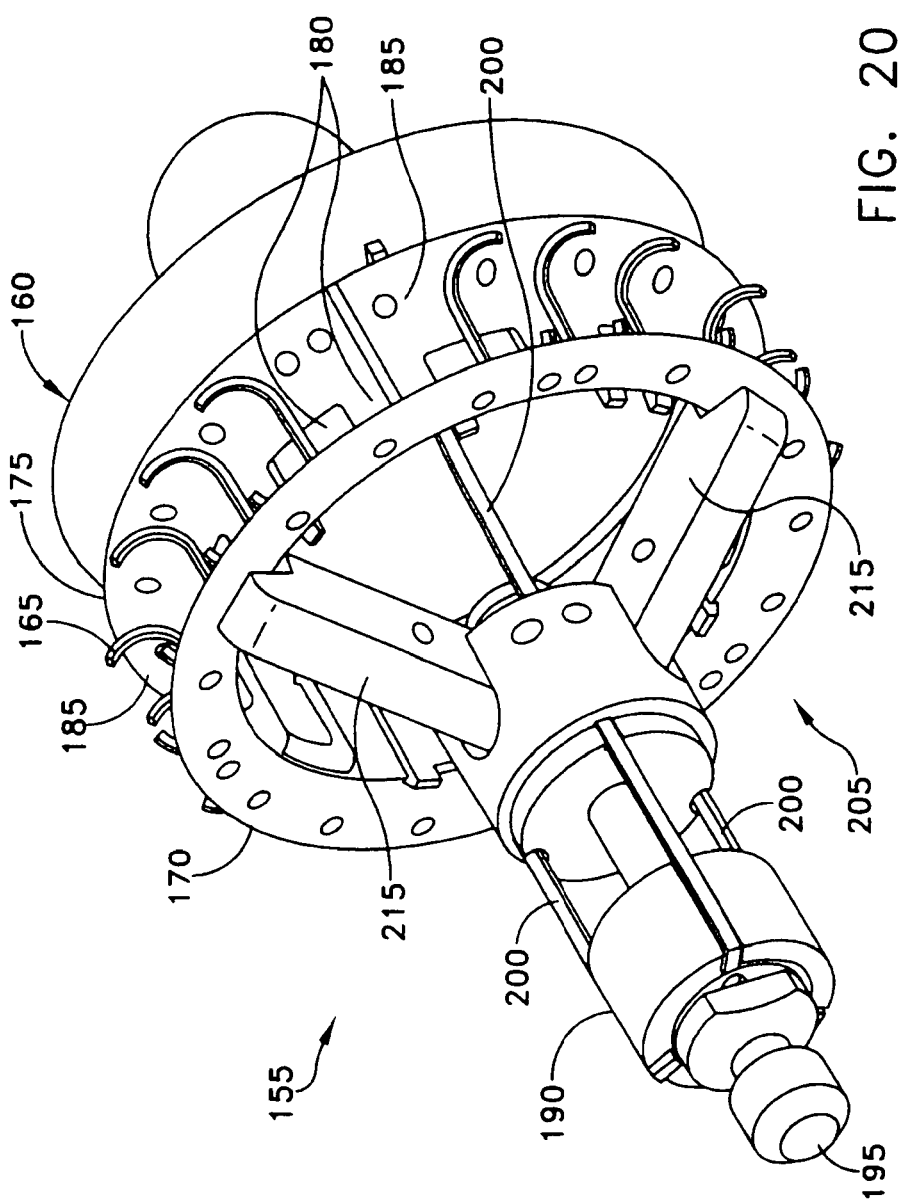

Looking next at FIGS. 19 and 20, apparatus 155 is shown subsequent to actuation, with top ring 170 and bottom ring 175 having been brought toward one another. In this configuration, staples 165 are deployed in a "C" configuration, extending away from each anvil 185, as top ring 170 and bottom ring 175 are drawn together. This deployment is effected by moving handle 195 away from support 205 (while applying a force on support 205 to prevent it from also moving with handle 195) so that cables 200 pull bottom ring 175 toward top ring 170, which is held stationary by legs 215.

Figure 21:
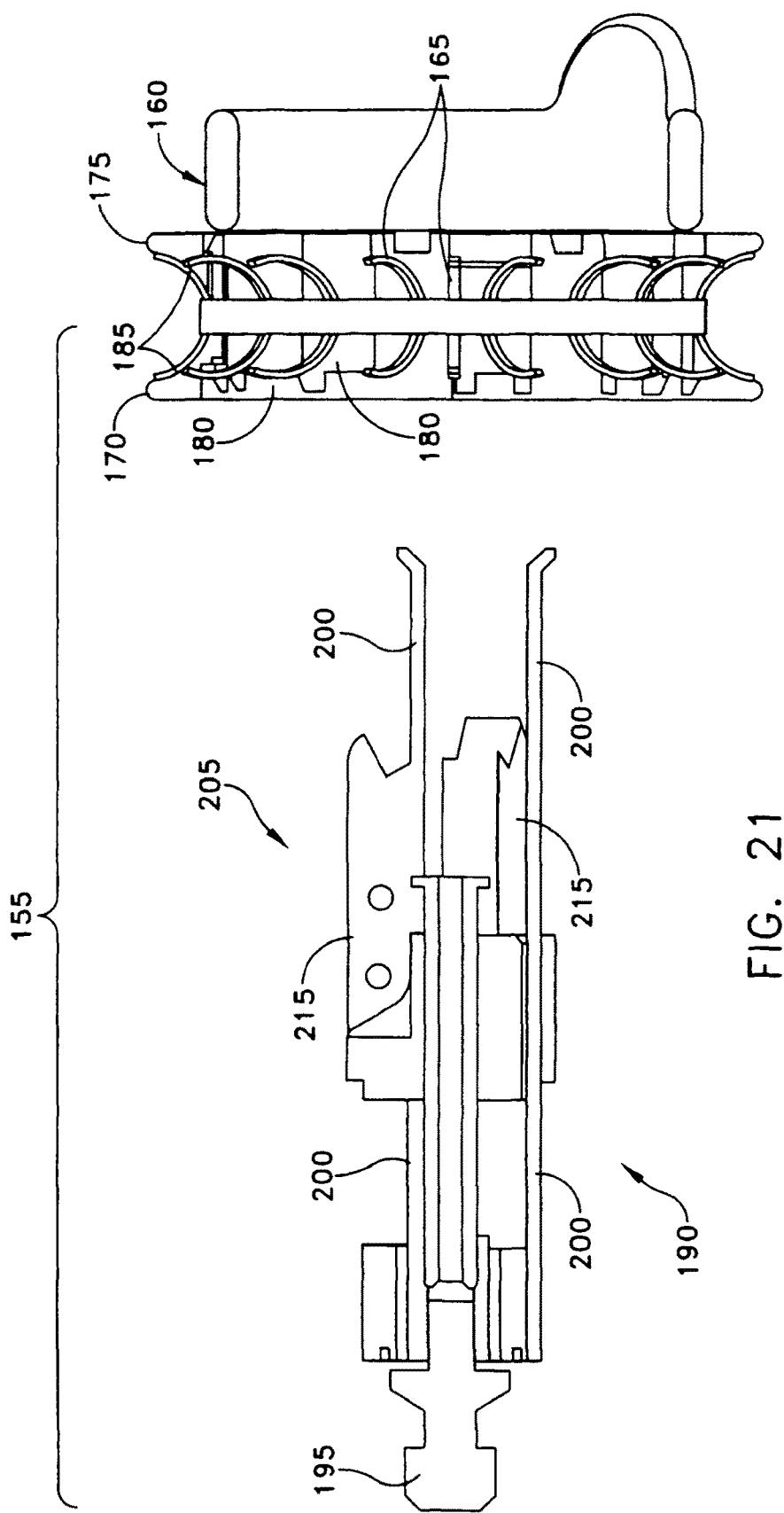
Figure 22:
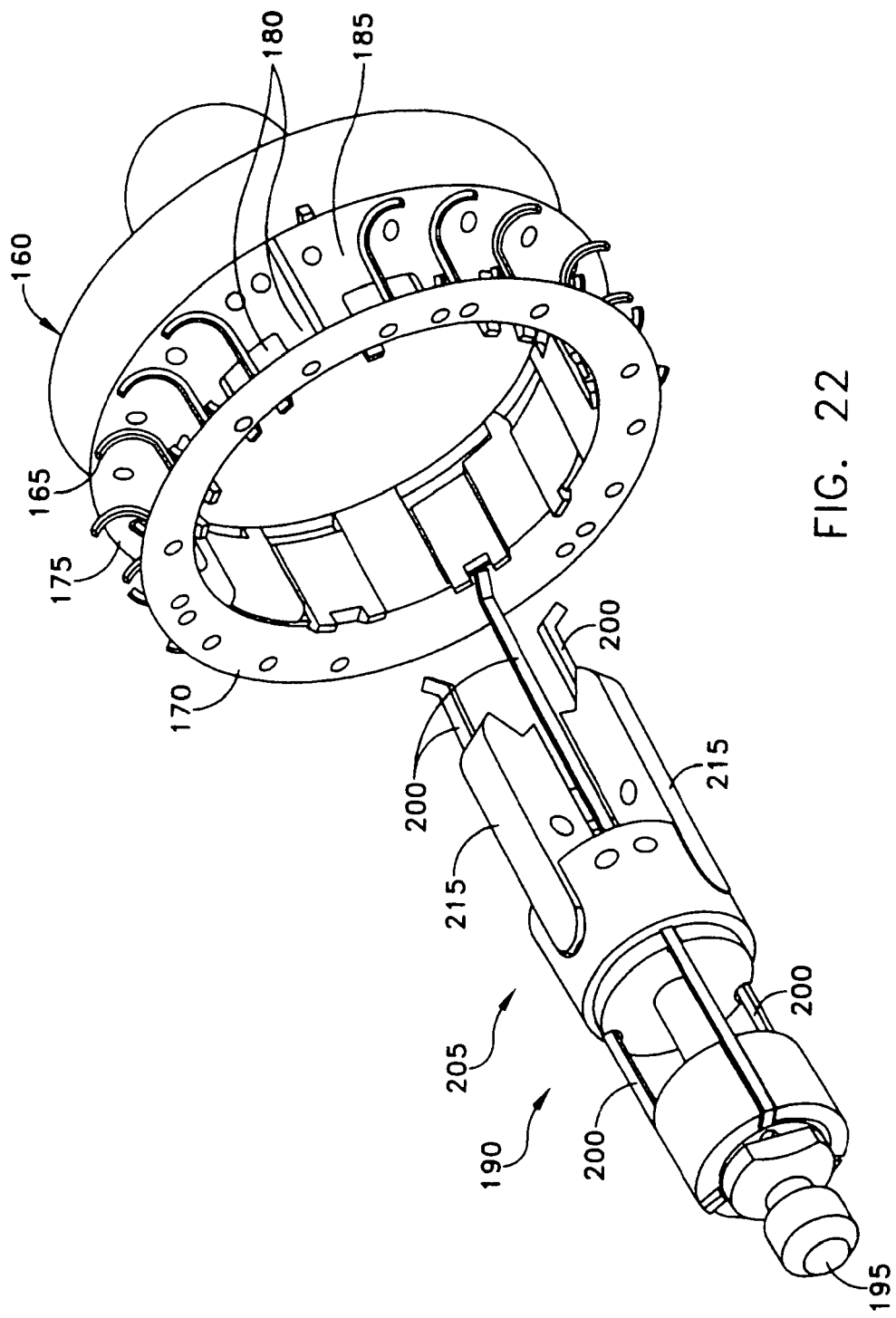

Looking now at FIGS. 21 and 22, deployment means 190 are shown disconnected from apparatus 155 and prosthetic aortic valve 160, with apparatus 155 shown configured for attachment at or adjacent to the annulus of a native aortic heart valve (not shown). Deployment means 190 is configured to disengage from apparatus 155 when handle 195 is moved away from apparatus 155 without holding support 205 stationary; as this occurs, cables 200 withdraw from bottom ring 175 and legs 215, which are pivotally attached together, collapse so that they can be withdrawn through a narrow opening.

Figure 23:
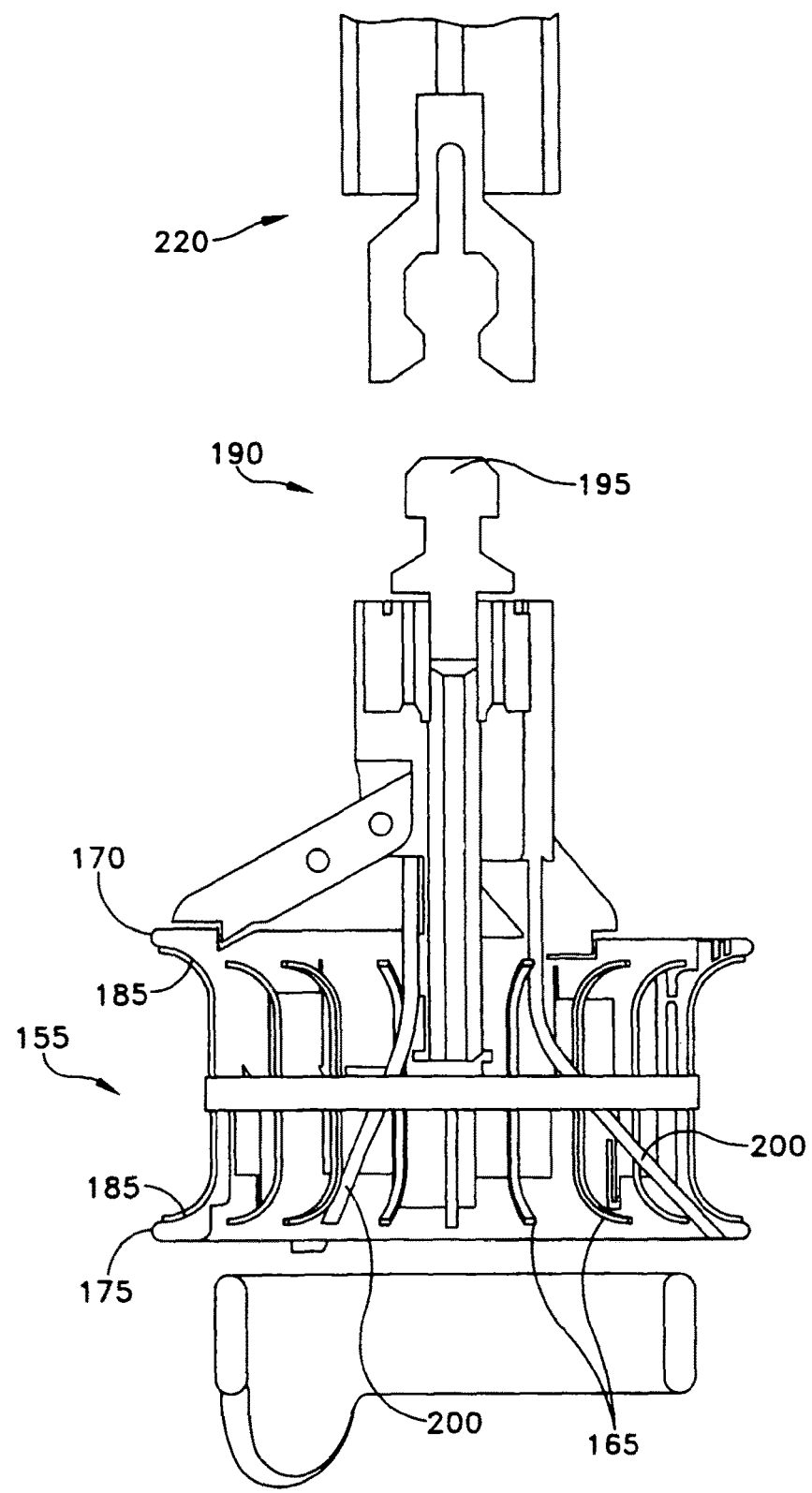
Figure 24:
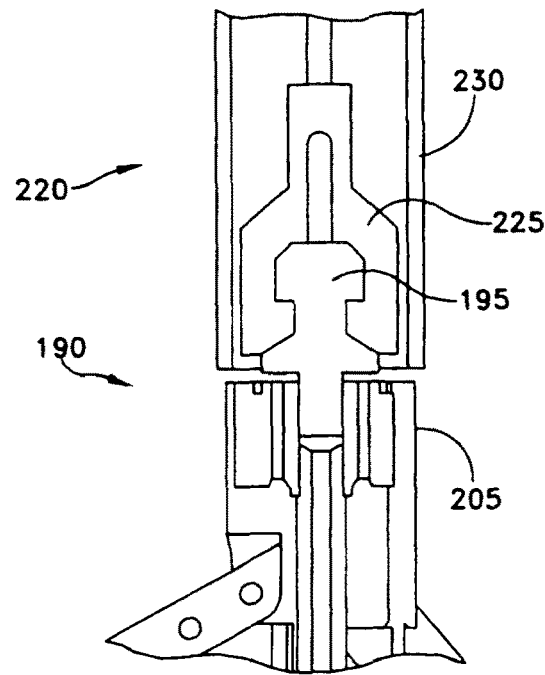
Figure 25:
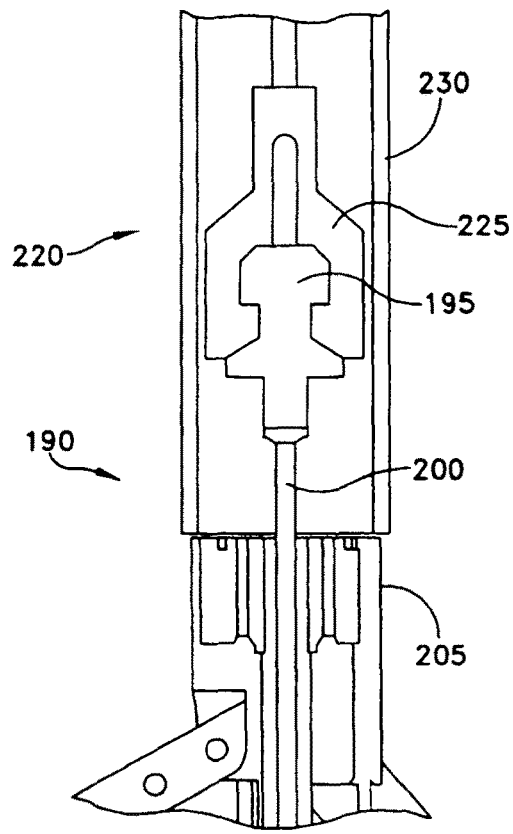
Figure 26:
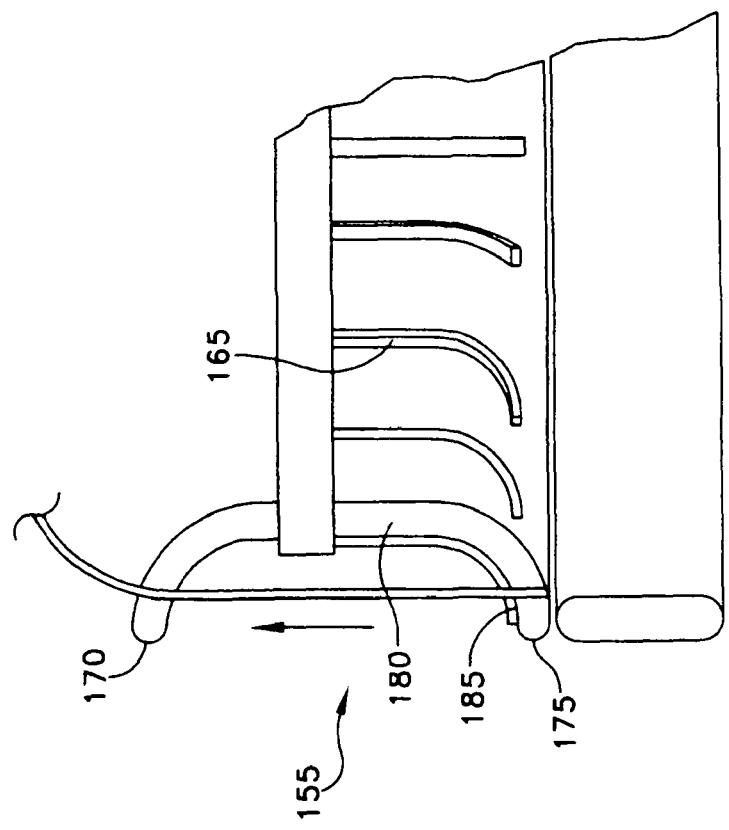
Figure 29:
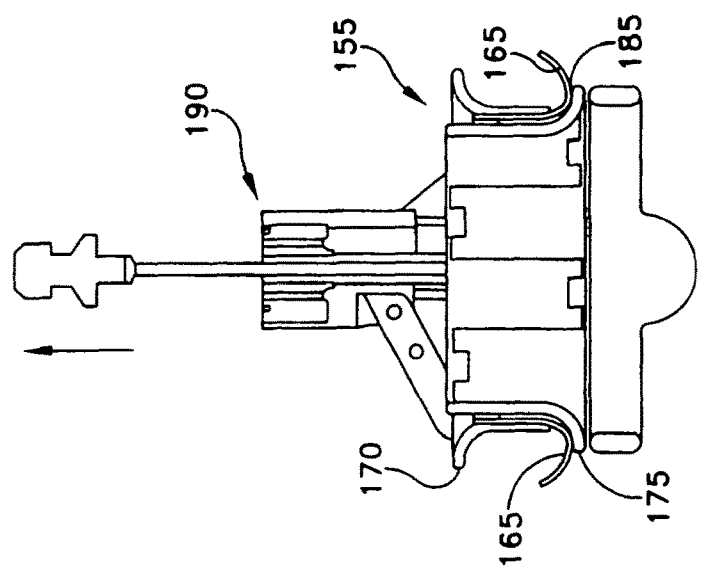
Figure 28:
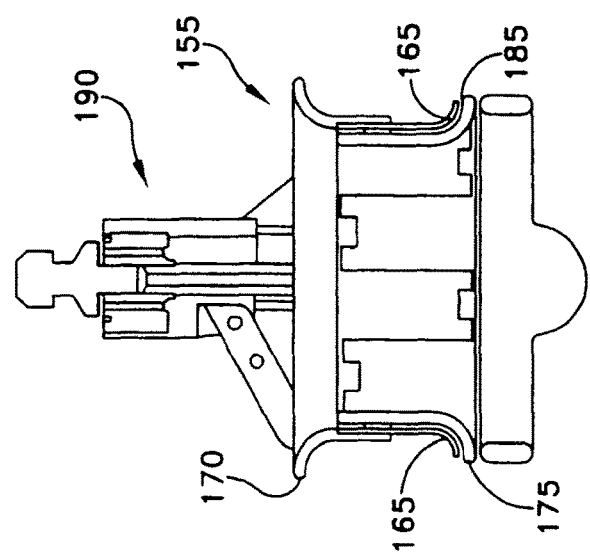
Figure 27:
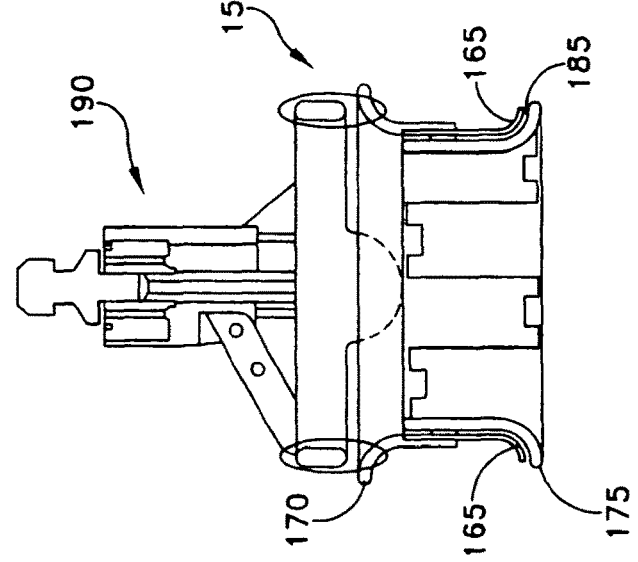

Looking next at FIGS. 23-25, apparatus 155 is shown being actuated by a tubular controller 220. Tubular controller 220 generally comprises a grasper 225 for selective attachment to handle 195, and a tube 230 surrounding grasper 225 for selectively engaging support 205. When compression apparatus 155 is to be deployed (i.e., when it is to have its rings 170 and 175 drawn together so as to deform the staples 165), tube 230 is held against support 205 while grasper 225 pulls handle 195 away from support 205. When deployment means 190 are to be withdrawn from compression apparatus 155, tubular controller is withdrawn from compression apparatus 155 by simultaneously withdrawing both grasper 225 and tube 230.

Referring now to FIGS. 26-29, there is shown apparatus 155 having a single-anvil 185 for forming staple 165 into a "half-c" configuration. In this embodiment, apparatus 155 may be configured with a height of about half that of an apparatus 155 that forms a "C" configuration.

Figure 30:
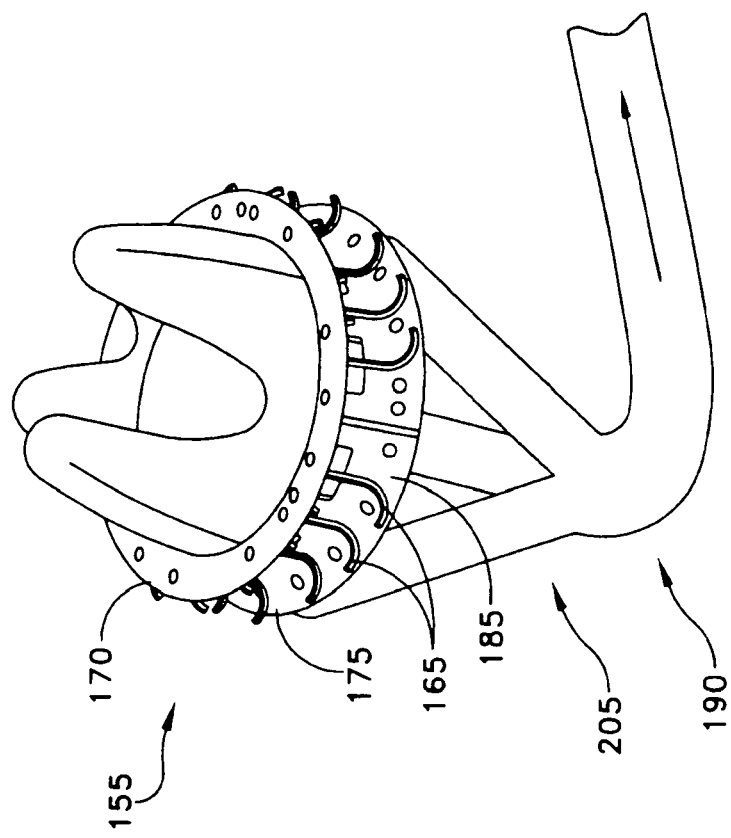
Figure 31:
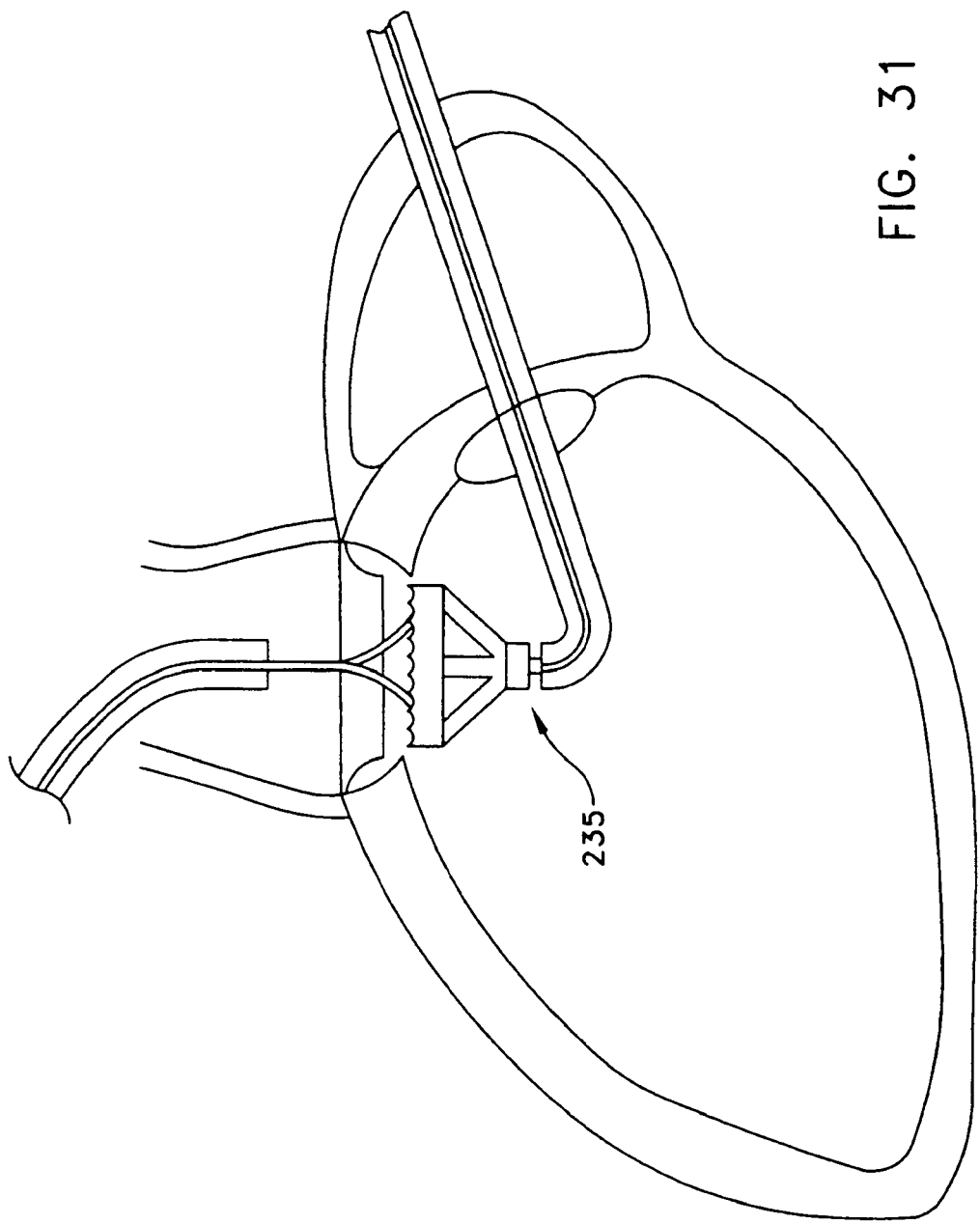
FIGS. 31 and 32 are schematic views showing a heart valve replacement using a left ventrical approach.
Figure 32:
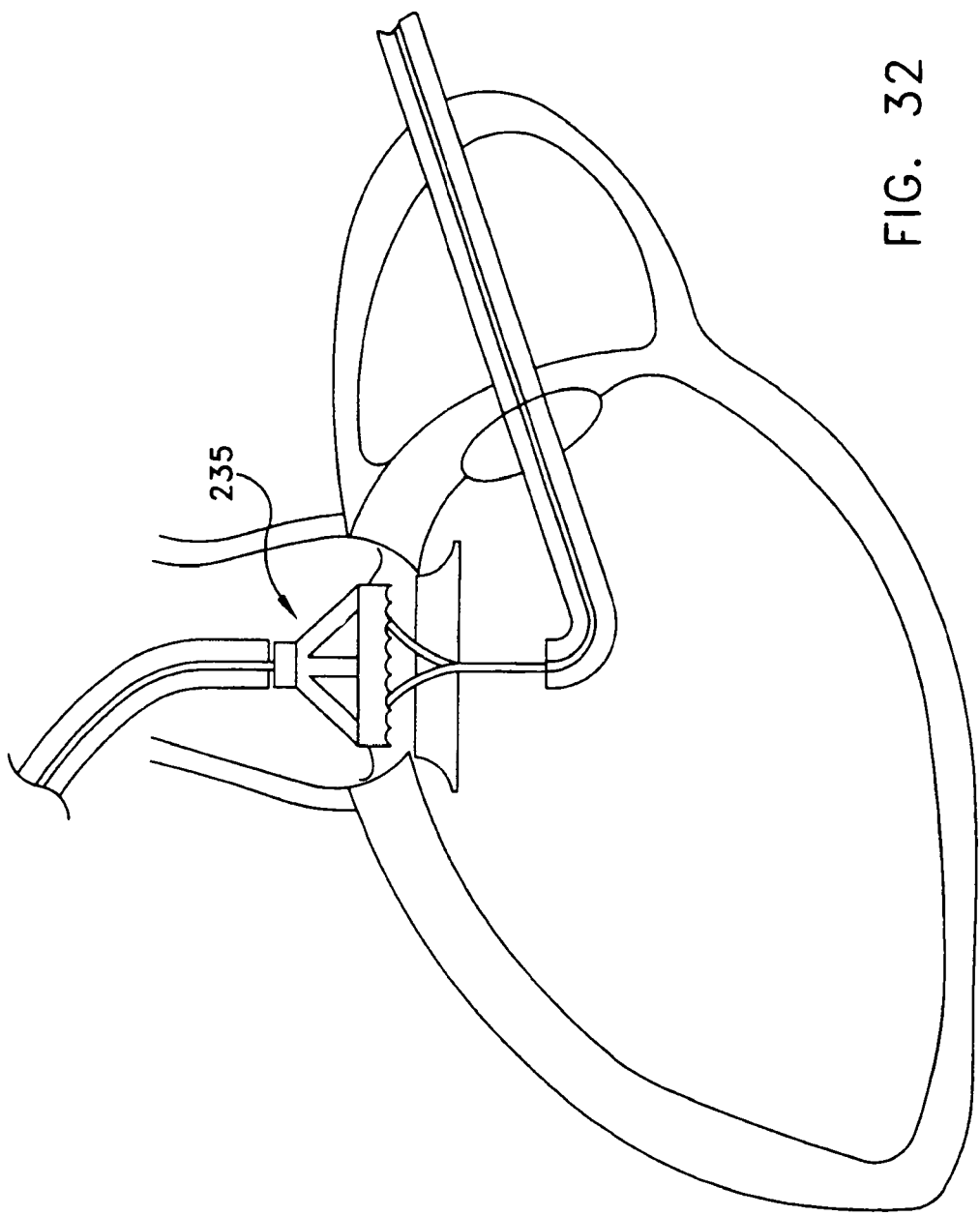
Figure 38:
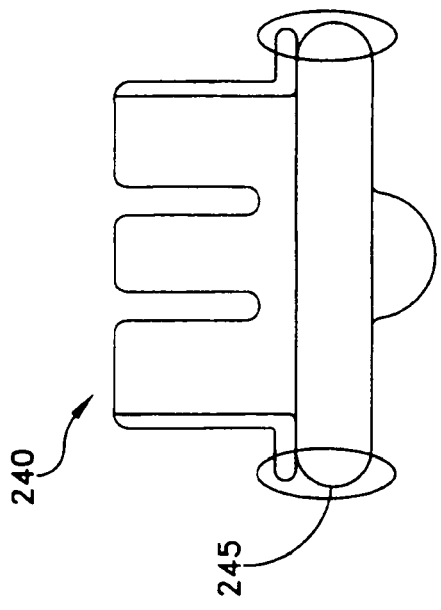
Figure 39:
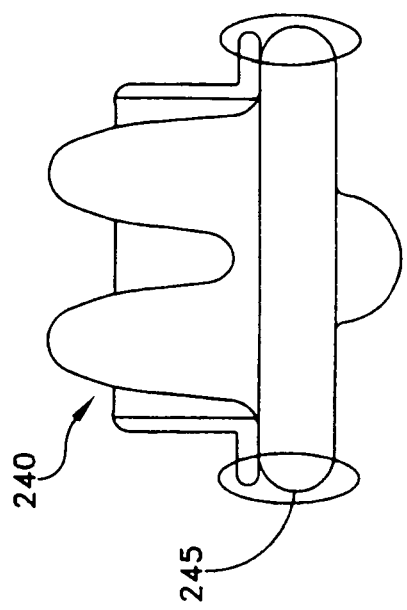
Figure 37:
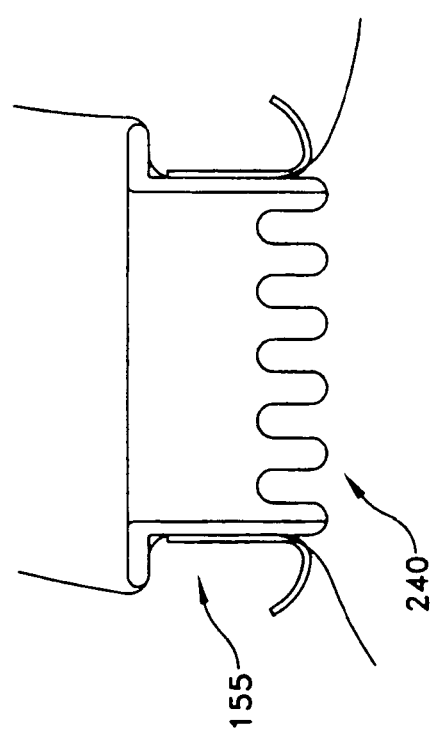
Figure 40:
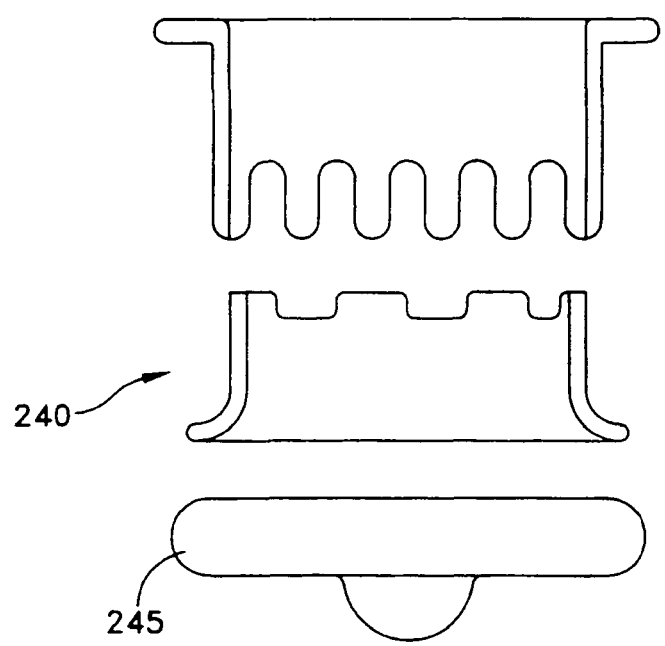
FIG. 40 is a schematic view showing another embodiment of a prosthetic heart valve using snap fit means.

Looking now at FIGS. 30-32, in a preferred embodiment of the present invention, there is shown apparatus being placed super-annular, i.e., on the aorta side of the aortic valve. This placement of apparatus 155 superior to the annulus is preferably performed using a left ventricle approach through the heart. For such a procedure, a collapsible support 205 may be used. Alternatively, a non-collapsible support (not shown) may be used. As shown in FIGS. 31 and 32, a punch 235 may be used to resect the native aortic valve, with the punch approaching from either a left ventricle approach (FIG. 31) or an aortic approach (FIG. 32).

Looking at FIGS. 33-35, in a preferred embodiment of the present invention, there is shown apparatus 155 being affixed to the annulus of the native heart valve. In this embodiment, staples 165 are placed at the annulus so as to hold apparatus 155 in place.

Looking next at FIG. 36, a fixation ring 237 is shown with snap fit means 238 for attachment of a prosthetic valve 239 to the fixation ring 237. Fixation ring 237 is deployed adjacent to the annulus of the native aortic valve and prosthesis 239 is snap fit to fixation ring 237 using snap fit means 238.

Looking next at FIGS. 37-40, in a preferred embodiment of the present invention, there is shown apparatus 155 configured with spring snaps 240 for attachment of a prosthesis 245 to apparatus 155. Prosthesis 245 may be secured to apparatus 155 after attachment of apparatus 155 to the annulus is completed.

In the preceding description, compressive apparatus 155 is described in the context of affixing a prosthetic heart valve in position within the aorta. In this respect it should be appreciated, however, that compressive apparatus 155 may be used to affix some other heart valve within another cardiovascular structure.

Still other modifications and variations will be apparent to those skilled in the art in view of the present disclosure, and are considered to be within the scope of the present invention.

What is claimed is:

1. A prosthetic heart valve comprising:
  a tube defining a proximal end, a distal end, and a central lumen;
  a tubular frame being disposed on an outside wall of the tube, the tubular frame comprising:
    a plurality of longitudinally-extending members, each having a hook at a distal end thereof; and
    at least one laterally-extending member fixed to the longitudinally-extending members, the laterally-extending member extending circumferentially relative to the longitudinally-extending members;
  the distal end of the tube being everted around the distal end of the tubular frame and extending proximally along the tubular frame and over the hooks to be engaged thereby; wherein the distal end of the tube comprises a radially-extending flange; wherein one laterally-extending member is at least partially positioned outside of the tube; and
  a valve member attached to the tube.

2. The prosthetic heart valve of claim 1 wherein the hooks are configured to secure the tubular frame to tissue.

3. The prosthetic heart valve of claim 1 wherein the at least one laterally-extending member comprises a circular hoop configuration.

4. The prosthetic heart valve of claim 1 wherein the at least one laterally-extending member comprises a serpentine configuration.

5. The prosthetic heart valve of claim 1 wherein the distal end of the tube is flared outwardly.

6. A prosthetic heart valve comprising:
  a tube defining a proximal end, a distal end, and a central lumen;
  a tubular frame defining a proximal end, a distal end, and a central lumen, the tubular frame being disposed on an outside wall of the tube the tubular frame comprising:
    a plurality of longitudinally-extending members, each having a hook at a distal end thereof; wherein the proximal end of each longitudinally-extending member comprises a fixation element for securing the tubular frame to tissue; and
    at least one laterally-extending member fixed to the longitudinally-extending members, the laterally-extending member extending circumferentially relative to the longitudinally-extending members;
  the distal end of the tube being everted around the distal end of the tubular frame and extending proximally along the tubular frame and over the hooks to be engaged thereby; wherein one laterally-extending member is at least partially positioned outside of the tube; and
  a valve member attached to the tube.

7. The prosthetic heart valve of claim 6 wherein the fixation element is configured to be bent radially outward to engage tissue.

8. The prosthetic heart valve of claim 6 further comprising a restraining device, wherein the fixation element is adapted to be deployed by removing the restraining device, whereby the fixation element automatically deploys to engage tissue.

9. A prosthetic heart valve comprising:
a tube defining a proximal end, a distal end, and a central lumen;
a tubular frame defining a proximal end, a distal end, and a central lumen, the tubular frame being disposed on an outside wall of the tube, the tubular frame further comprising a plurality of radially-extending members; wherein the tubular frame further comprises a plurality of longitudinally-extending members having a distal end and a proximal end; wherein the proximal end of each longitudinally-extending member is positioned outside of the everted tube; wherein the tubular frame further comprises at least one laterally-extending member fixed to the longitudinally-extending members, the laterally-extending member extending circumferentially relative to the longitudinally-extending members; wherein the proximal end of each longitudinally-extending member comprises a fixation element for securing the tubular frame to tissue;
the distal end of the tube being everted around the distal end of the tubular frame and extending proximally along the tubular frame and over the radially-extending members; wherein the tubular frame is at least partially positioned outside of the everted tube; and
a valve member attached to the tube.

10. The prosthetic heart valve of claim 9 wherein the at least one laterally-extending member comprises a circular hoop configuration.

11. The prosthetic heart valve of claim 9 wherein the at least one laterally-extending member comprises a serpentine configuration.

12. The prosthetic heart valve of claim 9 wherein the fixation element is configured to be bent radially outward to engage tissue.

13. The prosthetic heart valve of claim 9 further comprising a restraining device, wherein the fixation element is adapted to be deployed by removing the restraining device, whereby the fixation element automatically deploys to engage tissue.

14. The prosthetic heart valve of claim 9 wherein each radially-extending member comprises a hook configured to secure the tubular frame to tissue.

15. The prosthetic heart valve of claim 9 wherein the distal end of the tube is flared outwardly.

16. The prosthetic heart valve of claim 9 wherein the distal end of the tube comprises a radially-extending flange.

* * * * *